(12) United States Patent
Graves et al.

(10) Patent No.: US 8,564,776 B2
(45) Date of Patent: *Oct. 22, 2013

(54) SYSTEM AND METHOD FOR MEASURING PARTICLES IN A SAMPLE STREAM OF A FLOW CYTOMETER USING A LOW POWER LASER SOURCE

(75) Inventors: Steven W. Graves, San Juan Pueblo, NM (US); Robert C. Habbersett, Santa Fe, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/903,003

(22) Filed: Oct. 12, 2010

(65) Prior Publication Data
US 2011/0032522 A1   Feb. 10, 2011

Related U.S. Application Data

(63) Continuation of application No. 11/593,312, filed on Nov. 3, 2006, now Pat. No. 7,835,000.

(51) Int. Cl.
*G01N 21/00*   (2006.01)

(52) U.S. Cl.
USPC ........................................................ 356/338

(58) Field of Classification Search
USPC .................. 356/338, 73; 382/173; 250/458.1; 73/570.5; 3/338, 73
See application file for complete search history.

(56) References Cited

U.S. PATENT DOCUMENTS

| | | | |
|---|---|---|---|
| 2,900,536 | A | 8/1959 | Palo |
| 3,882,732 | A | 5/1975 | Fletcher et al. |
| 4,055,491 | A | 10/1977 | Porath-Furedi |
| 4,265,124 | A | 5/1981 | Lim et al. |
| 4,285,810 | A | 8/1981 | Kirkland et al. |
| 4,350,683 | A | 9/1982 | Galfre et al. |

(Continued)

FOREIGN PATENT DOCUMENTS

| | | |
|---|---|---|
| CN | 1493831 A | 5/2004 |
| CN | 1524948 | 9/2004 |

(Continued)

OTHER PUBLICATIONS

Aboobaker, N. et al., "Mathematical modeling of the movement of suspended particles subjected to acoustic and flow fields", App. Math. Modeling, 2005, 29, 515-532.

(Continued)

*Primary Examiner* — Tarifur Chowdhury
*Assistant Examiner* — Michael P LaPage
(74) *Attorney, Agent, or Firm* — Woodcock Washburn, LLP

(57) ABSTRACT

A system and method for analyzing a particle in a sample stream of a flow cytometer or the like. The system has a light source, such as a laser pointer module, for generating a low powered light beam and a fluidics apparatus which is configured to transport particles in the sample stream at substantially low velocity through the light beam for interrogation. Detectors, such as photomultiplier tubes, are configured to detect optical signals generated in response to the light beam impinging the particles. Signal conditioning circuitry is connected to each of the detectors to condition each detector output into electronic signals for processing and is designed to have a limited frequency response to filter high frequency noise from the detector output signals.

15 Claims, 12 Drawing Sheets

(56) References Cited

U.S. PATENT DOCUMENTS

| | | | |
|---|---|---|---|
| 4,434,230 A | 2/1984 | Ritts, Jr. | |
| 4,492,752 A | 1/1985 | Hoffman et al. | |
| 4,523,682 A | 6/1985 | Barmatz et al. | |
| 4,523,982 A | 6/1985 | Lee | |
| 4,596,464 A * | 6/1986 | Hoffman et al. | 356/336 |
| 4,604,542 A | 8/1986 | Thompson | |
| 4,673,512 A | 6/1987 | Schram | |
| 4,743,361 A | 5/1988 | Schram | |
| 4,759,775 A | 7/1988 | Peterson et al. | |
| 4,777,823 A | 10/1988 | Barmatz et al. | |
| 4,790,653 A * | 12/1988 | North, Jr. | 356/73 |
| 4,845,025 A | 7/1989 | Lary et al. | |
| 4,867,559 A | 9/1989 | Bach | |
| 4,877,516 A | 10/1989 | Schram | |
| 4,913,883 A | 4/1990 | Imai et al. | |
| 4,964,303 A | 10/1990 | Barmatz et al. | |
| 4,979,824 A | 12/1990 | Mathies et al. | |
| 4,987,086 A | 1/1991 | Brosnan et al. | |
| 4,991,923 A | 2/1991 | Kino et al. | |
| 5,006,266 A | 4/1991 | Schram | |
| 5,030,002 A | 7/1991 | North, Jr. | |
| 5,032,381 A | 7/1991 | Bronstein et al. | |
| 5,040,890 A | 8/1991 | North, Jr. | |
| 5,079,959 A | 1/1992 | Miyake et al. | |
| 5,085,783 A | 2/1992 | Feke et al. | |
| 5,106,187 A * | 4/1992 | Bezanson | 356/73 |
| 5,164,094 A | 11/1992 | Stuckart | |
| 5,225,089 A | 7/1993 | Benes et al. | |
| 5,264,906 A | 11/1993 | Ferer et al. | |
| 5,346,670 A | 9/1994 | Renzoni et al. | |
| 5,376,551 A | 12/1994 | Yoshikami | |
| 5,395,588 A | 3/1995 | North, Jr. et al. | |
| 5,430,541 A | 7/1995 | Sapp | |
| 5,491,344 A | 2/1996 | Kenny et al. | |
| 5,504,337 A | 4/1996 | Lakowicz et al. | |
| 5,527,460 A | 6/1996 | Trampler et al. | |
| 5,528,045 A | 6/1996 | Hoffman et al. | |
| 5,547,849 A | 8/1996 | Baer et al. | |
| 5,626,767 A | 5/1997 | Trampler et al. | |
| 5,644,388 A | 7/1997 | Maekawa et al. | |
| 5,674,698 A | 10/1997 | Zarling et al. | |
| 5,688,406 A | 11/1997 | Dickinson et al. | |
| 5,690,895 A * | 11/1997 | Matsumoto et al. | 422/73 |
| 5,711,888 A | 1/1998 | Trampler et al. | |
| 5,739,902 A | 4/1998 | Gjelsnes et al. | |
| 5,798,222 A | 8/1998 | Goix | |
| 5,800,861 A | 9/1998 | Chiang et al. | |
| 5,831,166 A | 11/1998 | Kozuka et al. | |
| 5,915,925 A | 6/1999 | North | |
| 5,981,180 A | 11/1999 | Chandler et al. | |
| 6,003,388 A | 12/1999 | Oeftering | |
| 6,055,859 A | 5/2000 | Kozuka et al. | |
| 6,074,879 A | 6/2000 | Zelmanovic et al. | |
| 6,090,295 A | 7/2000 | Raghavarae et al. | |
| 6,197,593 B1 | 3/2001 | Deka et al. | |
| 6,216,538 B1 | 4/2001 | Yasuda et al. | |
| 6,221,258 B1 | 4/2001 | Feke et al. | |
| 6,228,652 B1 * | 5/2001 | Rodriguez et al. | 436/63 |
| 6,248,590 B1 | 6/2001 | Malachowski | |
| 6,255,118 B1 | 7/2001 | Alfano et al. | |
| 6,309,886 B1 | 10/2001 | Ambrose et al. | |
| 6,332,541 B1 | 12/2001 | Coakley et al. | |
| 6,348,687 B1 | 2/2002 | Brockmann et al. | |
| 6,373,567 B1 | 4/2002 | Wise et al. | |
| 6,449,563 B1 | 9/2002 | Dukhin et al. | |
| 6,467,350 B1 | 10/2002 | Kaduchak et al. | |
| 6,532,061 B2 * | 3/2003 | Ortyn et al. | 356/28 |
| 6,549,275 B1 | 4/2003 | Cabuz et al. | |
| 6,565,727 B1 | 5/2003 | Shenderov et al. | |
| 6,592,821 B1 | 7/2003 | Wada et al. | |
| 6,604,435 B2 | 8/2003 | Buchanan et al. | |
| 6,644,118 B2 | 11/2003 | Kaduchak et al. | |
| 6,647,739 B1 | 11/2003 | Kim | |
| 6,668,664 B1 | 12/2003 | Ohkawa | |
| 6,683,314 B2 | 1/2004 | Oostman, Jr. et al. | |
| 6,713,019 B2 | 3/2004 | Ozasa et al. | |
| 6,736,904 B2 | 5/2004 | Poniatowski et al. | |
| 6,773,556 B1 | 8/2004 | Brockie et al. | |
| 6,794,671 B2 * | 9/2004 | Nicoli et al. | 250/574 |
| 6,797,158 B2 | 9/2004 | Feke et al. | |
| 6,813,017 B1 | 11/2004 | Hoffman et al. | |
| 6,816,257 B2 | 11/2004 | Goix | |
| 6,831,279 B2 | 12/2004 | Ho | |
| 6,881,314 B1 | 4/2005 | Wang et al. | |
| 6,911,082 B2 | 6/2005 | Sato et al. | |
| 6,929,750 B2 | 8/2005 | Laurell et al. | |
| 6,949,355 B2 | 9/2005 | Yamanishi et al. | |
| 7,008,540 B1 | 3/2006 | Weavers et al. | |
| 7,018,819 B2 | 3/2006 | Orwar et al. | |
| 7,047,809 B2 | 5/2006 | Cobb | |
| 7,052,864 B2 | 5/2006 | Durkop et al. | |
| 7,064,823 B2 * | 6/2006 | Roche et al. | 356/246 |
| 7,081,192 B1 | 7/2006 | Wang et al. | |
| 7,091,348 B2 | 8/2006 | O'Neill et al. | |
| 7,108,137 B2 | 9/2006 | Lal et al. | |
| 7,113,266 B1 * | 9/2006 | Wells | 356/73 |
| 7,161,665 B2 | 1/2007 | Johnson | |
| 7,255,780 B2 | 8/2007 | Shenderov | |
| 7,262,838 B2 | 8/2007 | Fritz | |
| 7,315,357 B2 | 1/2008 | Ortyn et al. | |
| 7,329,545 B2 | 2/2008 | Pamula et al. | |
| 7,340,957 B2 | 3/2008 | Kaduchak et al. | |
| 7,362,432 B2 | 4/2008 | Roth | |
| 7,373,805 B2 | 5/2008 | Hawkes et al. | |
| 7,403,125 B2 | 7/2008 | Rich | |
| 7,431,892 B2 | 10/2008 | Zumeris et al. | |
| 7,477,363 B2 | 1/2009 | Nagai | |
| 7,570,676 B2 | 8/2009 | Essaian et al. | |
| 7,758,811 B2 | 7/2010 | Durack et al. | |
| 7,990,525 B2 | 8/2011 | Kanda | |
| 2003/0059850 A1 | 3/2003 | Evans | |
| 2003/0086608 A1 * | 5/2003 | Frost et al. | 382/173 |
| 2003/0098421 A1 * | 5/2003 | Ho | 250/458.1 |
| 2003/0235919 A1 * | 12/2003 | Chandler | 436/43 |
| 2004/0065599 A1 | 4/2004 | Lal et al. | |
| 2004/0069717 A1 | 4/2004 | Laurell et al. | |
| 2005/0072677 A1 | 4/2005 | Gascoyne et al. | |
| 2005/0097968 A1 | 5/2005 | Ishikawa et al. | |
| 2006/0006769 A1 | 1/2006 | Masters et al. | |
| 2006/0021437 A1 * | 2/2006 | Kaduchak et al. | 73/570.5 |
| 2006/0034733 A1 | 2/2006 | Ferren et al. | |
| 2006/0071580 A1 | 4/2006 | Sawada | |
| 2006/0163166 A1 | 7/2006 | Hawkes et al. | |
| 2007/0037172 A1 * | 2/2007 | Chiu et al. | 435/6 |
| 2007/0071683 A1 | 3/2007 | Dayton et al. | |
| 2007/0098232 A1 | 5/2007 | Matula et al. | |
| 2007/0119239 A1 | 5/2007 | Priev et al. | |
| 2007/0263693 A1 * | 11/2007 | Essaian et al. | 372/75 |
| 2008/0053787 A1 | 3/2008 | Bagajewicz | |
| 2008/0106736 A1 | 5/2008 | Graves et al. | |
| 2008/0245709 A1 | 10/2008 | Kaduchak et al. | |
| 2008/0245745 A1 | 10/2008 | Ward et al. | |
| 2009/0029870 A1 | 1/2009 | Ward et al. | |
| 2009/0038932 A1 | 2/2009 | Denslow et al. | |
| 2009/0042239 A1 | 2/2009 | Ward et al. | |
| 2009/0042310 A1 | 2/2009 | Ward et al. | |
| 2009/0045107 A1 | 2/2009 | Ward et al. | |
| 2009/0048805 A1 | 2/2009 | Kaduchak et al. | |
| 2009/0050573 A1 | 2/2009 | Ward et al. | |
| 2009/0053686 A1 | 2/2009 | Ward et al. | |
| 2009/0107241 A1 | 4/2009 | Goddard et al. | |
| 2009/0139332 A1 | 6/2009 | Goddard et al. | |
| 2009/0158823 A1 | 6/2009 | Kaduchak et al. | |
| 2009/0162887 A1 | 6/2009 | Kaduchak et al. | |
| 2009/0178716 A1 | 7/2009 | Kaduchak et al. | |
| 2009/0227042 A1 | 9/2009 | Gauer et al. | |
| 2009/0316151 A1 | 12/2009 | Matula et al. | |
| 2010/0000325 A1 | 1/2010 | Kaduchak et al. | |
| 2010/0009333 A1 | 1/2010 | Auer | |

(56) References Cited

U.S. PATENT DOCUMENTS

| | | | |
|---|---|---|---|
| 2011/0024335 | A1 | 2/2011 | Ward et al. |
| 2011/0134426 | A1 | 6/2011 | Kaduchak et al. |

FOREIGN PATENT DOCUMENTS

| | | |
|---|---|---|
| CN | 1739020 A | 2/2006 |
| CN | 101060898 | 10/2007 |
| DE | 3027433 | 2/1982 |
| EP | 0 147 032 | 3/1985 |
| EP | 0 292 470 | 11/1988 |
| EP | 0 773 055 | 5/1997 |
| EP | 1 416 239 | 5/2004 |
| FR | 821419 | 12/1937 |
| GB | 500271 | 12/1937 |
| JP | 363139231 | 6/1988 |
| JP | 01-112161 | 4/1989 |
| JP | 406241977 | 9/1994 |
| JP | 408266891 | 10/1996 |
| JP | 11-014533 | 1/1999 |
| RU | 2224992 | 2/2004 |
| WO | WO 88/09210 | 12/1988 |
| WO | WO 90/05008 | 5/1990 |
| WO | WO 94/29695 | 12/1994 |
| WO | WO 97/02482 | 1/1997 |
| WO | WO 99/42810 | 8/1999 |
| WO | WO 00/41794 | 7/2000 |
| WO | WO 02/072234 | 9/2002 |
| WO | WO 02/072236 | 9/2002 |
| WO | WO 02/072236 A2 | 9/2002 |
| WO | WO 03/079006 | 9/2003 |
| WO | WO 2004/024287 | 3/2004 |
| WO | WO 2004/033087 | 4/2004 |
| WO | WO 2004/048948 | 6/2004 |
| WO | WO 2006/031299 | 3/2006 |
| WO | WO 2006/032703 | 3/2006 |
| WO | WO 2006/076195 A2 | 7/2006 |
| WO | WO 2007/128795 | 11/2007 |
| WO | WO 2008/122051 | 10/2008 |
| WO | WO 2009/086043 | 7/2009 |
| WO | WO 2009/091925 | 7/2009 |
| WO | WO 2011/068764 A2 | 6/2011 |

OTHER PUBLICATIONS

Aleksandrov, et al., "Pulsed Laser Florescence Spectrometer," Zhurnal Prikladnoi Spektroskopii 47(4), Oct. 1987, pp. 686-692.
Anderson, M. et al., "The Physics and Technology of Ultrasonic Particle Separation in Air", WCU, 2003, 1615-1621.
Apfel, R.E. et al., "Acoustic Radiation Pressure—Principles and Application to Separation Science", Fortschritte Der Akustik DAGA '90, 1990, 19-30.
Araz, M.K. et al., "Ultrasonic Separation in Microfluidic Capillaries", IEEE Ultrasonics Symposium, 2003, 1066-1069.
Asai, K. et al., "Ultrasonic treatment of slurry", Third International Coal Preparation Conference, 1958, 518-527.
Bardsley, et al., "Electroacoustic Productions of Murine Hybridomas," Journal of Immunological Methods, 129(1), (no month available) 1990, pp. 41-47.
Barmatz, M. et al., "Acosutic radiation potential on a sphere in plane, cylindrical, and spherical standing wave fields", J. Acoust. Soc. Am., 1985, 77, 928-945.
Bauerecker, S. et al., "Formation and growth of ice particles in stationary ultrasonic fields", J. of Chem. Phys., 1998, 3709-3712.
Bazou, D. et al., "Physical Environment of 2-D Animal Cell Aggregates Formed in a Short Pathlength Ultrasound Standing Wave Trap", Ultrasound in Med. & Biol., 2005, 31, 423-430.
Benes, E. et al., "Abscheidung Dispergierter Teilchen Durch Ultraschall-Induzierte Koagulation", Taauna der Deutschen Arbeitsaameinschaft fur Akustik—DAGA '89, 1989, 1-4.
Benes, E. et al., "Improved quartz crystal microbalance technique", J. Appl. Phys., 1984, 56, 608-626.

Beverloo, H.B. et al., "Inorganic Phsophors as New Luminescent Labels for Irnmunocytochernistry and Time-Resolved Microscopy", Cytometry, 1990, 11, 784-792.
Bienvenue, J.M. et al., "Microchip-Based Cell Lysis and DNA Extraction from Sperm Cells for Application to Forensic Analysis", J. Forensic Sci., 2006, 51, 266-273.
Binks, B.P. et al., "Modern Aspects of Emulsion Science", The Royal Society of Chemistry, 1998, 310-321.
Bishop, J.E. et al., "Mechanism of higher brightness of PerCP-Cy5. 5", Cytometry Supp, 2000, 10, 162-163.
Borgnis, "Acoustic Radiation Pressure of Plane Compressional Waves," Reviews of Modern Physics 25( 3), Jul. 1953, pp. 653-664.
Borisov, S.M. et al., "Blue LED Excitable Temperature Sensors Based ona New Eurpium (III) Chelate," J. Fluoresc., 2008, 18,581-589.
Borthwick, K.A. et al., "Development of a novel compact sonicator for cell disruption", J. of Microbioloaical Methods, 2005, 60, 207-216.
Bosma, R. et al., "Ultrasound, a new separation technique to harvest microlalgae", J. Appl. Phycology, 2003, 15, 143-153.
Bossuyt, X. et al., "Comparative Analysis for Whole Blood Lysis Methods for Flow Cytometry", Cytometry, 1997, 30, 124-133.
Brodeur, P. H., "Acoustic Separation in a Laminar Flow," Ultrasonics Symposium, 1994, pp. 1359-1362.
Caperan, P.H. et al., "Acoustic Agglomeration of a Glycol Fog Aerosol: Influence of Particle Concentration and Intensity of the Sound Field at Two Frequencies", J. Aerosol Sci., 1995, 26, 595-612.
Chase, E.S. et al., "Resolution of Dimly Fluorescent Particles: A Practical Measure of Fluorescence Sensitivity", Cytometry, 1998, 33, 267-279.
Cheung, et al., "Impedance Spectroscopy Flow Cytometry: On-Chip Label-Free Cell Differentiation," Cytometry Part A 65A, Feb. 10, 2005, pp. 124-132.
Coakley, W.T. et al., "Analytical scale ultrasonic standing wave manipulation of cells and microparticles", Ultrasonics, 2000, 38, 638-641.
Coakley, W.T. et al., "Cell-cell contact and membrane spreading in an ultrasound trap", Colloids and Surfaces B: Biointerfaces, 2004, 34, 221-230.
Coakley, W.T. et al., "Ultrasonic separations in analytical biotechnology", Tibtech, 1997, 15, 506-511.
Condrau, M.A. et al., "Time-Resolved Flow Cytometry for the Measurement of Lanthanide Chelate Fluorescence: I. Concept and Theoretical Evaluation", Cytometry, 1994, 16, 187-194.
Condrau, M.A. et al., "Time-Resolved Flow Cytometry for the Measurement of Lanthanide Chelate Fluorescence: II. Instrument Design and Experimental Results", Cytometry, 1994, 16, 195-205.
Cousins, C.M. et al., "Plasma Preparation from Whole Blood Using Ultrasound", Ultrasound in Med. & Biol., 2000, 26, 881-888.
Curtis, H.W. et al., "Ultrasonic Continuous Flow Plasmapheresis Separator", IBM Tech. Disc. Bulletin, 1982, 25,192-1 93.
Czyz, H. et al., "On the Concentration of Aerosol Particles by Means of Drift Forces in a Standing Wave Field", Acustica, 1990, 70, 23-28.
Dain, Y. et al., "Dynamics of Suspended Particles in a Two-Dimensional High-Frequency Sonic Field", J. Aerosol Sci., 1995, 26, 575-594.
Dain, Y. et al., "Side drift of aerosols in two-dimensional resonant acoustic levitators", J. Acoust. Soc. Am, 1997, 102, 2549-2555.
Danilov, S D. et al., "Mean force on a small sphere in a sound field in a viscous fluid", J. Acoust. Soc. Am., 2000, 107, 143-1 53.
Danilov, S.D. et al., "The Mean Force Acting on a Small Body in an Axisymmetric Sound Field in a Real Medium", Izvestiva Adademii Nauk SSSR, Mekhanika Zhidkosti I Gaza, 1985, 5, 812-820.
Dean, P.N. et al., "Hydrodynamic Orientation of Sperm Heads for Flow Cytometry", Biophys. J., 1978, 23, 7-13.
Doblhoff-Dier, 0. et al., "A Novel Ultrasonic Resonance Field Device for the Retention of Animal Cells", Biotechnol. Prog., 1994, 10, 428-432.
Doinikov, A.A. et al., "Acoustic radiation force on a spherical particle in a viscous heat-conducting fluid. I. General formula", J. Acoust. Soc. Am., 1997, 101, 713-721.

(56) References Cited

OTHER PUBLICATIONS

Doinikov, A.A. et al., "Acoustic radiation force on a spherical particle in a viscous heat-conducting fluid. II. Force on a rigid sphere", J. Acoust. Soc. Am., 1997, 101, 722-730.

Doinikov, A.A. et al., "Acoustic radiation force on a spherical particle in a viscous heat-conducting fluid. III. Force on a liquid drop", J. Acoust. Soc. Am., 1997, 101, 731-740.

Doinikov, A.A. et al., "Acoustic radiation pressure on a rigid sphere in a viscous fluid", Proc. R. Soc. Lond., 1994, 447-466.

Donnert, G. et al., "Major signal increase in fluorescence microscopy through dark-state relaxation", Nature Methods, 2007, 4, 81-86.

Doornbos, R.M. et al., "Experimental and Model Investigations of Bleaching and Saturation of Fluorescence in Flow Cytometry", Cytometry, 1997, 29,204-214.

EPO Application No. EP 08733084: Extended European Search Report dated Mar. 24, 2010.

Fenniri, H. et al., "Classification of Spectroscopically Encoded Resins by Raman Mapping and Infrared Hyperspectral Imaging", Journal of Combinatorial Chemistry, 2006, 8, 192-198.

Fulwyler, M.J. et al., "Hydronamic Orientation of Cells", Histochem. Cytoche., 1977, 7, 781-783.

Gaida, T.H. et al., "Selective Retention of Viable Cells in Ultrasonic Resonance Field Devices", Biotech. Prog., 1996, 12, 73-76.

Gao, X. et al., "Quantum Dot-Encoded Mesoporous Beads with High Brightness and Uniformity: Rapid Readout Using Flow Cytometry", Anal. Chem., 2004, 3, 2406-2410.

Gherardini, L. et al., "A New Immobilisation Method to Arrange Particles in a Gel Matrix by Ultrasound Standing Waves", Ultrasound in Med. & Biol., 1005, 31, 261-272.

Goddard, G. et al., "Single Particle High Resolution Spectral Analysis Flow Cytometry", Cytometry, 2006, 69A, 842-851.

Goddard, G. et al., "Ultrasonic particle concentration in a line-driven cylindrical tube", J. Acoust. Soc. Am., 2005, 117, 3440-3447.

Goddard, G. et al., "Ultrasonic Particle-Concentration for Sheathless Focusing of Particles for Analysis in a Flow Cytometer", Cytometry, 2006, 69, 66-74.

Goddard, G.R. et al., "Ultrasonic Concentration in a Line Driven Cylindrical Tube", Dissertation, 2004, 1-276.

Gonzalez, I. et al., "Precise Measurements of Particle Entertainment in a Standing-Wave Acoustic Field Between 20 and 3500 Hz", J. Aerosol Sci., 2000, 31,1461-1 468.

Gor'Kov, L.P. et al., "On the forces acting on a small particle in an acoustical field in an ideal fluid", Soviet Physics-Doklady, 1962, 6, 773-775.

Gould, R.K. et al., "The effects of acoustic forces on small aprticles in suspension", Proceedings of the 1973 Symposium on Finite Amplitude Wave Effects in Fluids, Bjorno, L., ed., Pergamon, Guildford, 1974, 252-257.

Gould, R.K. et al., "Upper sound pressure limits on particle concentration in fields of ultrasonic standing-wave at megahertz frequencies", Ultrasonics, 1992, 30, 239-244.

Groschl, M. et al., "Automatische Frequenzregelung fur Piezoelektrische Resonatoren und deren Implementierung in akustischen Driftwellenresonator", Diplomarbeit Institut fur Allaemeine Phvsik, Technishchen Universitat Wien, 1991, 1-132.

Grossner, M.T. et al., "Single fiber model of particle retention in an acoustically driven porous mesh", Ultrasonics, 2003, 41, 65-74.

Grossner, M.T. et al., "Single-Collector Experiments and Modeling of Acoustically Aided Mesh Filtration", Amer. Inst. of Chem. Eng., 2005, 51, 1590-1598.

Grossner, M.T. et al., "Transport analysis and model for the performance of an ultrasonically enhanced filtration process", Chem. Ena. Sci., 2005, 60, 3233-3238.

Gupta, S. et al., "Acoustically driven collection of suspended particles within porous media", Ultrasonics, 1997, 35, 131-139.

Gupta, S. et al., "Fractionation of Mixed Particulate Solids According to Compressibility Using Ultrasonic Standing Wave Fields", Chem. Eng. Sci., 1995, 50, 3275-3284.

Haake, A. et al., "Contactless micromanipulation of small particles by an ultrasound field excited by a vibrating body", J. Acoust. Soc. Am., 2005, 117, 2752-2760.

Haake, A. et al., "Manipulation of Cells Using an Ultrasonic Pressure Field", Ultrasound in Med. & Biol., 2005, 31, 857-864.

Haake, A. et al., "Positioning of small particles by an ultrasound field excited by surface waves", Ultrasonics, 2004, 42, 75-80.

Haake, et al., "Positioning, Displacement, and Localization of Cells Using Ultrasonic Forces," Biotechnology and Bioengineering, 92(1), Aug. 10, 2005, pp. 8-14.

Habbersett, R.C. et al., "An Analytical System Based on a Compact Flow Cytometer for DNA Fragment Sizing and Single Molecule Detection", Cytometry 2004, 60A,125-134.

Hager, F. et al., "A Summary of All Forces Acting on Spherical Particles in a Sound Field", Proc. of the Ultrasonic International '91 Conference and Exhibition, Le Touauet, France, 1991, 1-4.

Hamilton, M.F. et al., "Acoustic streaming generated by standing waves in two-dimensional channels of arbitrary width", J. Acoust. Soc. Am., 2003, 113, 153-160.

Hamilton, M.F. et al., "Linear and nonlinear frequency shifts in acoustical resonators with varying cross sections", J. Acoust. Soc. Am., 2001, 110, 109-119.

Hancock, A., "Observation of Forces on Microparticles in Acoustic Standing Waves", Thesis, submitted in partial satisfaction of the reaquirements for the degree of Master of Science in Biomedical Engineering, University of California, Davis, 2001, 1-155.

Harma, H. et al., "Zeptomole detection sensitivity of prostate-specific antigen in a rapid microtitre plate assay using time-resolved fluorescence", Luminescence, 2000, 15, 351-355.

Harris, N.R. et al., "A silicon microfluidic ultrasonic separator", Sensors and Actuators, 2004, 95, 425-434.

Harrison, B.S. et al., "Near-Infrared Photo- and Electroluminescence of Alkoxy-Substituted Poly (p-phenylene) and Nonconjugated Polymer/Lanthanide Tetraphenylporphyrin Blends", Chemistrv of Materials, 2004, 16, 2938-2947.

Hatanaka, S-I et al., "Effect of Process Parameters on Ultrasonic Separation of Dispersed Particles in Liquid", Jpn. J. ADPI. Phvs., 1999, 38, 3096-3100.

Hawkes, et al., "Continuous Cell Washing and Mixing Driven by an Unitrsound Standing Wave Within a Microfluidic Channel," Lab Chip, 4, (no month available) 2004, pp. 446-452.

Hawkes, J.J. et al., "A laminar flow expansion chamber facilitating downstream manipulation of particles concentrated using an ultrasonic standing wave", Ultrasonics, 1998, 36, 901-903.

Hawkes, J.J. et al., "Force field particle filter, combinin ultrasound standing waves and laminar flow", Sensors and Actuators B, 2001, 75, 213-222.

Hawkes, J.J. et al., "Microparticle manipulation in millimetre scale ultrasonic standind wave chambers", Ultrasonics, 1998, 36, 925-931.

Hawkes, J.J. et al., "Single half-wavelength ultrasonic particle filter: Predictions of the transfer matrix multilayer resonator model and experimental filtration results", J. Acoust. Soc. Am., 2002, 111, 1259-1266.

Hawkes, J.J. et al., "Ultrasonic deposition of cells on a surface", Biosensors and Bioelectronics, 2004, 19,1021-1028.

Hemmila, I. et al., "Progress in Lanthanides as Luminescent Probes", J. Fluoresncence, 2005, 15, 529-542.

Hertz, H.M. et al., "Standing-wave acoustic trap for nonintrusive positioning of microparticles", J. Appl. Phys., 1995, 78, 4845-4849.

Higashitani, K.O. et al., "Migration of Suspended Particles in Plane Stationary Ultrasonic Field", Chem. Eng. Sci., 1981, 36, 1187-1192.

Hill M. et al., "Modelling in the design of a flow-through ultrasonic separator", Ultrasonics, 2000, 38, 662-665.

Hill M. et al., "Modelling of layered resonators for ultrasonic separation", Ultrasonics, 2002, 40, 385-392.

Hill, D.H. et al., "Operating Characteristics of Acoustically Driven Filtration Processes for Particulate Suspensions", Sep. Sci. and Tech., 2000, 35, 1363-1375.

Hill, M. et al., "The selection of layer thicknesses to control acoustic radiation forces profiles in layered resonators", J. Acoust. Soc. Am., 2003, 114(5), 2654-2661.

Hirschfeld, T. et al., "Fluorescence Background Discrimination by Prebleaching", J. Histochem. and Cytochem., 1979, 27, 96-101.

(56) References Cited

OTHER PUBLICATIONS

Holmes, D. et al., "High throughput particle analysis: Combining dielectrophoretic particle focussing with confocal optical detection", Biosensors and Bioelectronics, 2006, 21, 1621-1630.

Holwill, I.L. et al., "The use of ultrasonic standing waves to enhance optical particle sizing equipment", Ultrasonics, 2000, 38, 650-653.

Huhtinen, P. et al., "Synthesis, Characterization, and Application of Eu(III), Tb(III), Sm (III), and Dy(III) Lanthanide Chelate Nanoparticle Labels", Anal. Chem., 2005, 77, 2643-2648.

International Application No. PCT/US05/26524: International Search Report dated Oct. 3, 2006.

International Application No. PCT/US08/87579: International Search Report dated Feb. 9, 2009.

International Application No. PCT/US2008/059181: International Search Report dated Jul. 25, 2008.

International Application No. PCT/US2009/031154: International Search Report dated Jul. 8, 2009.

Invitrogen, "Fluo-4 NW Calcium Assay Kits (F36205, F36206)", Product Information, 2006.

Invitrogen, "Fluorophore selection guide for flow cytometry", Cellular Analvsis, 2007.

Johnston, P.A. et al., "Cellular platforms for HTS: three case studies", DDT, 2002, 7, 353-363.

Jonsson, H. et al., "Particle separation using ultrasound can be used with human shed mediastinal blodd", Perfusion, 2005, 20, 39-43.

Juarez, J.A. et al., "Piezoelectric Transducer for Air-Borne Ultrasound", Acustica, 1973, 29, 234-239.

Kaduchak, G. et al., "E6 diffraction catastrophe of the primary rainbow of oblate water drops: observations with white-light and laser illumination", Applied Optics, 1994, 33, 4691-4696.

Kaduchak, G. et al., "Hyperbolic umbilic and E6 diffraction catastrophes associated with the secondary rainbow of oblate water drops: observations with laser illumination", Applied Optics, 1994, 33, 4697-4701.

Kapishnikov, S. et al., "Continuous particle size separation and size sorting using ultrasound in a microchannel", J. Stat. Mech., 2006, 1-1 3.

Karumanchi, R.S. et al., "Field-assisted extraction of cells, particles and macromolecules", TRENDS is Biotech, 2002, 20, 72-78.

Kaye, P.H. et al., "Spatial light-scattering analysis as a means of characterizing and classifying non-spherical particles", Meas. Sci. Technol.,1998, 9, 141-149.

Keij, et al.,"Coincidence in High-Speed Flow Cytometry: Models and Measurements," Cytometry 12, Jan. 22, 1991, pp. 398-404.

Kilburn, D.G. et al., "Enhanced Sedimentation of Mammalian Cells following Acoustic Aggregation", Biotech. and Bioeng., 1989, 34, 559-562.

King, L.V. et al., "On the acoustic radiation on spheres", Proc. R. Soc. A., 1933, 147, 212-240.

Kogan, S. et al., "Acoustic concentration of particles in piezoelectric tubes: Theoretical modeling of the effect of cavity shape and symmetry breaking", J. Acoust. Soc. Am., 2004, 116, 1967-1974.

Kozuka, T. et al., "Acoustic Micromanipulation Using a Multi-Electrode Transducer", 7th Inter. Svmp. On Micro Machine and Human Science IEEE, 1996, 163-170.

Kozuka, T. et al., "Control of a Standing Wave Field Using a Line-Focused Transducer for Two-Dimensional Manipulation of Particles", Jpn. J. Appl. Phys., 1998, 37, 2974-2978.

Kozuka, T. et al., "Micromanipulation Using a Focused Ultrasonic Standing Wave Field", Electronics and Communications in Japan, 2000, 83, 1654-1659.

Kumar, M. et al., "Fractionation of Cell Mixtures Using Acoustic and Laminar Flow Fields", Biotech. Bioeng., 2005, 89, 129-137.

Kundt, A. et al., "Longitudinal vibrations and acoustic figures in cylindrical columns of liquids", Annalen der Physik and Chemie (Poggendorffs Annalen), 1874, 153, 1-12.

Kuznetsova, L.A. et al., "Cavitation buble-driven cell and particle behavior in a ultrasound standing wave", J. Acoust. Soc. Am., 2005, 117, 104-112.

Kuznetsova, L.A. et al., "Microparticle concentration in short path length ultrasonic resonators: Roles of radiation pressure and acoustic streaming", J. Acoust. Soc. Am., 2004, 116, 1956-1966.

Kwiatkowski, C.S. et al., "Resonator frequency shift due to ultrasonically induced microparticle migration in an aqueous suspension: Observations and model for the maximum frequency shift", J. Acoust. Soc. Am., 1998, 103, 3290-3300.

Lakowicz, J.R. et al., "On the Possibility of Long-Wavelength Long-Lifetime High-Quantum-Yield Luminophores", Analyical Biochemistry, 2001, 288, 62-75.

Leif, R.C. et al., "Increasing the Luminescence of Lanthanide Complexes", Cytometry, 2006, 69A, 767-778.

Leif, R.C. et al., "Markers for Instrumental Evaluation of Cells of the Female Reproductive Tract; Existing and New Markers", in the Automation of Uterine Cancer Cytology Tutorials of Cytology, (edited by G.L. Wied. et al.), 1976, 313-344.

Lierke, E.G. et al., "Acoustic Positioning for Space Processing of Materials Science Samples in Mirror Furnaces", IEEE Ultrasonics Symposium, 1983, 1129-1139.

Lilliehorn, T. et al., "Trapping of microparticles in the rear field of an ultrasonic transducer", Ultrasonics, 2005, 43, 293-303.

Lofstedt, R. et al., "Theory of long wavelength acoustic radiation pressure", J. Acoust. Soc. Am., 1991, 90, 2027-2033.

Loken, M.R. et al., "Cell Discrimination by Multiangle Light Scattering", Histochem. Cytochem., 1976, 24, 284-291.

Loken, M.R. et al., "Identification of Cell Asymmetry and Orientation by Light Scattering", Histochem. Cytochem., 1977, 7, 790-795.

Macey, M.G. et al., "Comparative Study of Five Commercial Reagents for Preparing Normal and Leikaemic Lymphoctyes for Immunophenotypic Analysis by Flow Cytometry", Cytometry, 1999, 38,153-160.

Maltsev, V.P. et al., "Scanning flow cytometry for individual particle analysis", Review of Scientific Instruments, 2000, 71, 243-255.

Mandralis, Z. et al., "Enhanced synchronized ultrasonic and flow-field fractionation of suspensions", Ultrasonics, 1994, 32, 113-121.

Mandralis, Z. et al., "Transient Response of Fine Particle Suspensions to Mild Planar Ultrasonic Fields", Fluid/Particle Separation J., 1990, 115-121.

Marston, P.L. et al., "Generalized rainbows and unfolded glories of oblate drops: organization for multiple internal reflection and extension of cusps into Alexander's dark band", Applied Optics, 1994, 33, 4702-4713.

Marston, P.L. et al., "Manipulation of Fluid Objects with Acoustic Radiation Pressure", Ann. N.Y. Acad. Sci., 2004, 1027, 414-434.

Marston, P.L. et al., "Resonances, Radiation Pressure, and Optical Scattering Phenomena of Drops and Bubbles", Proceedings of the Second International Colloquium on Drops and Bubbles, Jet Prop. Lab. Pub 82-7 Pasadena, CA, 1982, 166-174.

Marston, P.L., "Tensile Strength and Visible Ultrasonic Cavitation of Superfluid 4He*," Journal of Low Temperature Physics, 25(3/4), Mar. 5, 1976, pp. 383-407.

Martin, K.M. et al., "Acoustic filtration and sedimentation of soot particles", Experiments in Fluids, 1997, 23, 483-488.

Masudo, T. et al., "Particle Characterization and Separation by a Coupled Acoustic-Gravity Field", Analytical Chemistry 2001, 73, 3467-3471.

Mathies, R.A. et al., "Optimization of High-Sensitivity Fluorescence Detection", Anal. Chem., 1990, 62, 1786-1791.

Mazumdar, M.K. et al., "Single particle aerodynamic relaxation time analyzer", Rev. Sci. Instrum., 1977, 48, 622-624.

Mazumdar, M.K. et al., "Spart Analyzer: Its Application to Aerodynamic Size Distribution Measurement", J. Aerosol Sci., 1979, 10, 561-569.

McCartin, B.J., "A Numerical Procedure for 2D Acoustic Waveguides with Heated Walls", http://flux.aps.org/meetings/YR99/OSS99/abs/S700004.html, 1999.

Meindersma, G.W. et al., "Separation of a biocatalyst with ultrafiltration or filtration after bioconversion", J. Membrane Sci., 1997, 125, 333-349.

Morgan, J. et al., "Manipulation of in vitro toxicant sensors in an ultrasonic standing wave", Toxicology in Vitro, 2004, 18, 115-120.

Mullaney, P.F, et al., "The Small Angle Light Scattering of Biological Cells", Biophys. J., 1970, 10, 764-772.

(56) References Cited

OTHER PUBLICATIONS

Neild, A. et al., "Design, modeling and characterization of microfluidic devices for ultrasonic manipulation", Sensors and Actuators B: Chemical, Feb. 20, 2007, 121(2).
Neild, A., "A micro-particle positioning technique combining an ultrasound manipulator and a microgripper," J. Micromechanical Microengineering, 2006, 16, 1562-1570.
Neukammer, J. et al., "Angular distribution of light scattered by single biological cells and oriented particle agglomerates", Appl. Opt., 2003, 42, 6388-6397.
Nilsson, A. et al., "Acoustic control of suspended particles in micro fluidic chips", Lab Chip, 2004, 4, 131-135.
Nolan et al., "Suspension Array Technology: New Tools fro Gene and Protein Analysis", Cell and Molecular Biology, 2001, 47, 1241-1256.
Nowotny, H. et al., "Layered piezoelectric resonators with an arbitrary number electrodes (general one-dimensional treatment)", J. Acoust. Soc. Am., 1991, 90, 1238-1245.
Otaki, M. et al., "Virus Removal in a Membrane Separation Process", Water Sci. and Tech., 1998 37, 107-116.
Pangu, G.D. et al., "Acoustically aided separation of oil droplets from aqueous emulsions", Chem. Eng. Sci., 2004, 59, 3183-3193.
Petersson, F. et al., "Carrier Medium Exchange through Ultrasonic Particle Switching in Microfluidic Channels", Anal. Chem., 2005, 77, 1216-1221.
Petersson, F. et al., "Continuous separation of lipid particles from erythrocytes by means of laminar flow and acoustic standing wave forces", Lab Chip, 2005, 5, 20-22.
Petersson, F. et al., "Free Flow Acoustophoresis: Microfluidic-Based Mode of Particle and Cell Separation", Anal. Chem., 2007 79, 5117-5123.
Petersson, F., "Particle Flow Switch Utilizing Ultrasonic Particle Switching in Microfluidic Channels", 7th International Conf on Miniaturizing Chem and Biochem Analysis Systems, 2003, 879-882.
Pregibon, D.C. et al., "Multifunctional Encoded Particles for High-Throughput Biomolecule Analysis", Science, 2007, 315, 1393-1396.
Princen, K. et al., "Evaluation of SDF-1/CXCR4-Induced Ca2+Signaling by Fluorometric Imaging Plate Reader (FLIPR) and Flow Cytometry", Cytometry, 2003, 51A, 35-45.
Pui, P.W. et al., "Batch and Semicontinuous Aggregattion and Sedimentation of Hybridoma Cells by Acoustic Resonance Fields", Biotechnol. Prog., 1995, 11, 146-152.
Rama Rao, G.V. et al., "Monodisperse Mesoporous Silica Microspheres Formed by Evaporation-Induced Self Assembly of Surfacant Templates in Aerosols", Advanced Materials, 2002, 18,1301-1304.
Rens, W. et al., "A Novel Nouel for More Efficient Sperm Orientation to Improve Sorting Efficiency of X and Y Chromosome-Bearing Sperm", Cytometry, 1998, 33, 476-481.
Ricks, D.C. et al., "A numerically stable global matrix method for cylindrically layered shells excited by ring forces", J. Acoust. Soc. Am., 1994, 95, 3339-3349.
Rouleau, F. et al., "Electromagnetic scattering by compact clusters of spheres", Astron. Astrophys, 1996, 310, 686-698.
Rudnick, J. et al., "Oscillational instabilities in single-mode acoustic levitators", J. Acoust. Soc. Am., 1990, 87, 81-92.
Saito, M. et al., "Microorganism manipulation and microparticle arrangement by the use of ultrasonic standing waves", SPIE, 2001, 4590, 26-37.
Saito, M. et al., "Quantum mechanical representation of acoustic streaming and acoustic radiation pressure", Physical Review, 2001, E64, 026311-1-026311-5.
Saito, M. et al., "Ultrasonic manipulation of locomotive microorganisms and evaluation of their activity", J. App. Phvsics, 2002, 92, 7581-7586.
Saito, M. et al., "Ultrasonic trapping of paramecia and estimation of their locomotive force", Appl. Phys. Lett,1997, 71,1909-1911.
Saito, M. et al., "Ultrasonic waves for fabricating lattice structure in composite materials", SPIE, 1999, 3786, 179-190.

Samiotaki, M. et al., "Seven-Color Time-Resolved Fluorescence Hybridization Analysis of Human Papilloma Virus Types", Analytical Biochem., 1997, 253, 156-161.
Schmid, M. et al., "A computer-controlled system for the measurement of complete admittance spectra of piezoelectric resonators", Meas. Sci. Technol., 1990, 1, 970-975.
Schoell, W.M. et al., "Separation of Sperm and Vaginal Cells with Flow Cytometry for DNA Typing After Sexual Assault", Obstetrics and Gynecolony, 1999, 94, 623-627.
Semianov, K.A. et al., "Measurement of Mammalian Erythrocyte Indices from Light Scattering with Scaning Flow Cytometer", Proc. SPIE, 2003, 5141,106-113.
Sethu, P. et al., "Continuous Flow Microfluidic Device for Rapid Erythrocyte Lysis", Anal. Chem., 2004, 76, 6247-6253.
Shapiro, H.M. et al., Practical Flow Cytometry, Hoboken, NJ, John Wiley & Sons. Inc., 2005, 9-13.
Shvalov, A.N. et al., "Individual *Escherichia coli* Cells Studied from Light Scattering with the Scanning Flow Cytometer", Cytometry, 2000, 41, 41-45.
Shvalov, A.N. et al., "Light -scattering properties of individual erythrocytes", Applied Optics, 1999, 38, 230-235.
Simpson, H.J. et al., "Ultrasonic four-wave mixing mediated by an aqueous suspension of microspheres: Theoretical steady-state properties", J. Acoust. Soc. Am., 1995, 98, 1731-1741.
Skudrzyk, E. et al., "Die Grundlagen der Akustic", Sprinaer Verlaa. Wien, 1954, 202-205 and 807-825.
Slomkowski, S. et al., "New Types of Microspheres and Microsphere-related Materials for Medical Diagnostics", Polymers for Advanced Technologies, 2002, 13, 906-918.
Sobanski, M.A. et al., "Sub-micron particle manipulation in an ultrasonic standing wave: Applications in detection of clinically important biomolecules", Bioseparation, 2001, 9, 351-357.
Steinkamp, J.A. et al., "Dual-Laser, Differential Fluorescence Correction Method for Reducing Cellular Background Autofluorescence", Cytometry,1986, 7, 566-574.
Steinkamp, J.A. et al., "Enhanced Immunofluorescence Measurement Resolution of Surface Antigens on Highly Autofluorescent, Glutaraldehyde-Fixed Cells Analyzed by Phase-Sensitive Flow Cytometry", Cytometry, 1999, 37, 275-283.
Steinkamp, J.A., "A Differential Amplifier Circuit for Reducing Noise in Axial Light Loss Measurements", Cyometry, 1983, 4, 83-87.
Stewart, C.C. et al., "Resolving Leukocytes Using Axial Light Loss", Cytometry, 1989, 10, 426-432.
Stoffel, C.L. et al., "Data Analysis for a Dual Analysis for a Dual-Channel Virus Counter", Analytical Chemistry, 2005, 77, 2243-2246.
Stoffel, C.L. et al., "Design and Characterization of a Compact Dual Channel Virus Counter", Cytometry, 2005, Part A 65A, 140-147.
Stovel, R.T. et al., "A Means for Orienting Flat Cells in Flow Systems", Biophys J., 1978, 23, 1-5.
Takeuchi, J. et al., "Ultrasonic Micromanipulator Using Visual Feedback", Jpn J. Appl. Phys., 1996, 35, 3244-3247.
Takeuchi, M. et al., "Ultrasonic Micromanipulation of Small Particles in Liquid", Jpn J. Appl. Phys., 1994, 33, 3045-3047.
Thiessen, D.B. et al., "Principles of some Acoustical, Electrical, and Optical Manipulation Methods with Applications to Drops, Bubbles, and Capillary Bridges", ASME Fluids Eng. Div. Publ. FED, 1998.
Thiessen, D.B. et al., "Some Responses of Small Diffusion Flames to Ultrasonic Radiation", NASA, 2003, 321-324.
Tolt, T.L. et al., "Separation devices based on forced coincidence response of fluid-filled pipes", J. Acoust. Soc. Am., 1992, 91, 3152-3156.
Tolt, T.L. et al., "Separation of Dispersed Phases from Liquids in Acoustically Driven Chambers", Chem. Eng. Science, 1993, 48, 527-540.
Townsend, R.J. et al., "Modelling of particle paths passing through an ultrasonic standing wave", Ultrasonics, 2004, 42, 319-324.
Trihn, E.H. et al., "Experimental study of streaming flows associated with ultrasonic levitators", Phys. Fluids, 1994, 6, 3567-3579.
Trinh, E.H. et al., "Compact acoustic levitation device for studies in fluid dynamics and material science in the laboratory and microgravity", Rev. Sci. Instrum., 1985, 56, 2059-2065.
Tuckermann, R. et al., "Trapping of heavy gases in stationary ultrasonic fields", Chem. Phys. Ltrs., 2002, 363, 349-354.

(56) References Cited

OTHER PUBLICATIONS

Tung, Yi-C. et al., "PDMS-based opto-fluidic micro flow cytometer with two-color, multi-angle fluorescence detection capability using PIN photodiodes", Sensors and Actuators, 2004, 98, 356-367.
Tyson, D.S. et al., "Ruthenium (II) complex with a notably long excited state lifetime", The Royal Society of Chemistry, 2000, 2355-2356.
United States Patent and Trademark Office: Final Office Action dated Dec. 31, 2008, U.S. Appl. No. 11/784,936.
United States Patent and Trademark Office: Final Rejection dated Jul. 7, 2010, U.S. Appl. No. 11/784,928.
United States Patent and Trademark Office: Non-Final Office Action dated Jun. 10, 2010, U.S. Appl. No. 11/982,042.
United States Patent and Trademark Office: Non-Final Office Action dated Dec. 30, 2009, U.S. Appl. No. 11/784,928.
United States Patent and Trademark Office: Non-Final Office Action dated Apr. 3, 2008, U.S. Appl. No. 11/784,936.
United States Patent and Trademark Office: Non-Final Office Action dated Jun. 24, 2009, U.S. Appl. No. 11/784,936.
United States Patent and Trademark Office: Notice of Allowance dated Feb. 22, 2010, U.S. Appl. No. 11/784,936.
United States Patent and Trademark Office: Restriction Requirement dated Nov. 30, 2009, U.S. Appl. No. 11/982,042.
United States Patent and Trademark Office: Restriction Requirement dated Jul. 1, 2009, U.S. Appl. No. 11/784,928.
Vainshtein, P. et al., "On the Drift of Aerosol Particles in Sonic Fields", J. Aerosol Sci., 1992, 23, 631-637.
Vainshtein, P. et al., "The effect of centreline particle concentration in a wave tube", J. Fluid Mech., 1996, 306, 31-42.
Van Hee, P. et al., "Strategy for Selection of Methods for Separation of Bioparticles From Particle Mixtures", Biotech. Bioeng., 2006, 94, 689-709.
Verpoorte, E. et al., "Beads and chips: new recipes for analysis—Elisabeth Verpoorte reviews particle handling in microchannels", Lab Chip, 2003, 3, 60N-68N.
Visuri, S.V. et al., "Microfluidic tolls for biological sample preparation", Poster 1423, 2nd Annual International IEEE-EMBS Special Topic Cofnerence on Microtechnologies in Medicine & Biology, May 2-24, 2002 556-559.
Wang, Z. et al., "Retention and Viability Characteristics of Mammalian Cells in an Acoustically Driven Polymer Mesh", Biotechnol. Prog., 2004, 20, 384-387.
Ward, M. et al., "Manipulation of Immunomagnetic Targets in Microfluidic Channel Flow", Dissertation, 2005, 1-205.
Weiser, M.A. et al., "Interparticle Forces on Red Cells in a Standing Wave Field", Acustica, 1984, 56, 114-119.
Weiser, M.A.H. et al., "Extension of acoustic levitation to include the study of micron-size particles in a more compressible host liquid", J. Acoust. Soc. Am., 1982, 71, 1261-1268.
Whitworth, G. et al., "Particle column formation in a stationary ultrasonic field", J. Acoust. Soc. Am., 1992, 91, 79-85.
Whitworth, G. et al., "Transport and harvesting of suspended particles using modulated ultrasound", Ultrasonics, 1991, 29, 439-444.
Wu, Y. et al., "Diazo Coupling Method for Covalent Attachment of Proteins to Solid Substrates", Bioconjugate Chem., 2006, 17, 359-365.
Yagi, et al., "Flow Cytometry to Evaluate Theileria Sergenti Parasitemia Using the Florescent Nucleic Acid Stain SYTO16," Cytometry, 41, (no month available) 2000, pp. 223-225.
Yamakoshi, Y. et al., "Micro particle trapping by opposite phases ultrasonic travelling waves", Ultrasonics, 1998, 36, 873-878.
Yasuda, K. et al., "Blood Concentration by Superposition of Higher Harmonics of Ultrasound", Jpn. J. Appl. Phys., 1997, 36, 3130-3135.
Yasuda, K. et al., "Concentration and Fractionation of Small Particles in Liquid by Ultrasound", Jpn J. Appl. Phys., 1995, 34, 2715-2720.
Yasuda, K. et al., "Deoxyribonucleic acid concentration using acoustic radiation force", J. Acoust. Soc. Am., 1996, 99, 1248-1251.
Yasuda, K. et al., "Non-destructive, non-contact handling method for biomaterials in micro-chamber by ultrasound", Sensors and Actuators, 2000, 64, 128-135.
Yasuda, K. et al., "Particle separation using acoustic radiation force and elecrostatic force", J. Acoust. Soc. Am., 1996, 99, 1965-1970.
Yasuda, K. et al., "Using acousitc radiation force as a concentration method for erythrocytes", J. Acoust. Soc. Am., 1997, 102, 642-645.
Ye, C-H. et at., "Preparation of three terbium complexes with paminobenzoic acid and investigation of crystal structure influence on luminescence property", Journal of Solid State Chemistry, 2004, 177, 3735-3742.
Yosioka, K. et al., "Acoustic Radiation Pressure on a Comressible Sphere", Acustica, 1955, 5, 167-173.
Yuan, J. et al., "Lanthanide-based luminescence probes and time-resolved luminescence bioassays", Trends in Analytical Chernistry, 2006, 25, 490-500.
Yurkin, M.A. et al., "Experimental and theoretical study of light scattering by individual mature red blook cells by use of scanning flow cytometry and a discrete dipole approximation", Applied Optics, 2005, 44, 5249-5256.
Petersson et al., "Separation of Lipids from Blood Utilizing Ultrasonic Standing Waves in Microfluidic Channels," *Analyst*, 2004, 129, 938-943.
International Application No. PCT/US08/87579, Written Opinion dated Feb. 9, 2009.
U.S. Appl. No. 11/982,042: Final Office Action dated Sep. 24, 2010.
U.S. Appl. No. 11/982,042: Non-Final Office Action dated Mar. 4, 2011.
U.S. Appl. No. 11/593,312: Non-Final Office Action dated Oct. 16, 2008.
U.S. Appl. No. 11/593,312: Final Office Action dated May 13, 2009.
U.S. Appl. No. 11/593,312: Non-Final Office Action dated Oct. 23, 2009.
U.S. Appl. No. 11/593,312: Final Rejection dated Apr. 5, 2010.
U.S. Appl. No. 11/593,312: Notice of Allowance dated Jul. 6, 2010.
U.S. Appl. No. 11/593,312: Notice of Allowance dated Sep. 16, 2010.
U.S. Appl. No. 11/784,928: Notice of Allowance dated Dec. 13, 2010.
U.S. Appl. No. 11/784,936: Notice of Allowance dated May 28, 2010.
U.S. Appl. No. 11/784,936: Notice of Allowance dated Sep. 16, 2010.
U.S. Appl. No. 12/283,491: Restriction Requirement dated Jun. 25, 2010.
U.S. Appl. No. 12/283,491: Non-Final Office Action dated Sep. 27, 2010.
U.S. Appl. No. 12/283,491: Final Office Action dated Apr. 5, 2011.
U.S. Appl. No. 12/283,461: Restriction Requirement dated Jun. 28, 2010.
U.S. Appl. No. 12/283,461: Non-Final Office Action dated Sep. 28, 2010.
U.S. Appl. No. 12/283,461: Final Office Action dated Apr. 5, 2011.
Response to Mar. 24, 2010 Extended European Search Report in European Application No. 08733084.1 filed Jun. 16, 2010.
U.S. Appl. No. 11/982,042: Final Office Action dated Oct. 17, 2011.
U.S. Appl. No. 12/283,491: Non-Final Office Action dated Sep. 27, 2011.
U.S. Appl. No. 12/283,461: Non-Final Office Action dated Sep. 26, 2011.
U.S. Appl. No. 12/283,491: Ex parte Quayle Action dated Mar. 29, 2012.
U.S. Appl. No. 12/283,491: Notice of Allowance dated May 25, 2012.
U.S. Appl. No. 12/283,461: Ex parte Quayle Action dated Mar. 29, 2012.
U.S. Appl. No. 12/283,461: Notice of Allowance dated May 31, 2012.
U.S. Appl. No. 12/903,042: Non-Final Office Action dated May 11, 2012.
U.S. Appl. No. 13/295,934: Non-Final Office Action dated Oct. 9, 2012.
U.S. Appl. No. 12/903,042: Non-Final Office Action dated Nov. 15, 2012.
U.S. Appl. No. 12/903,042: Final Office Action dated May 24, 2013.
U.S. Appl. No. 13/295,934: Non-Final Office Action dated May 24, 2013.
Anderson, M.J. et al., "Use of Acoustic Radiation Pressure to Concentrate Small Particles in an Air Flow," 2002 IEEE Ultrasonics Symposium, Jan. 1, 2002, 481-484.

* cited by examiner

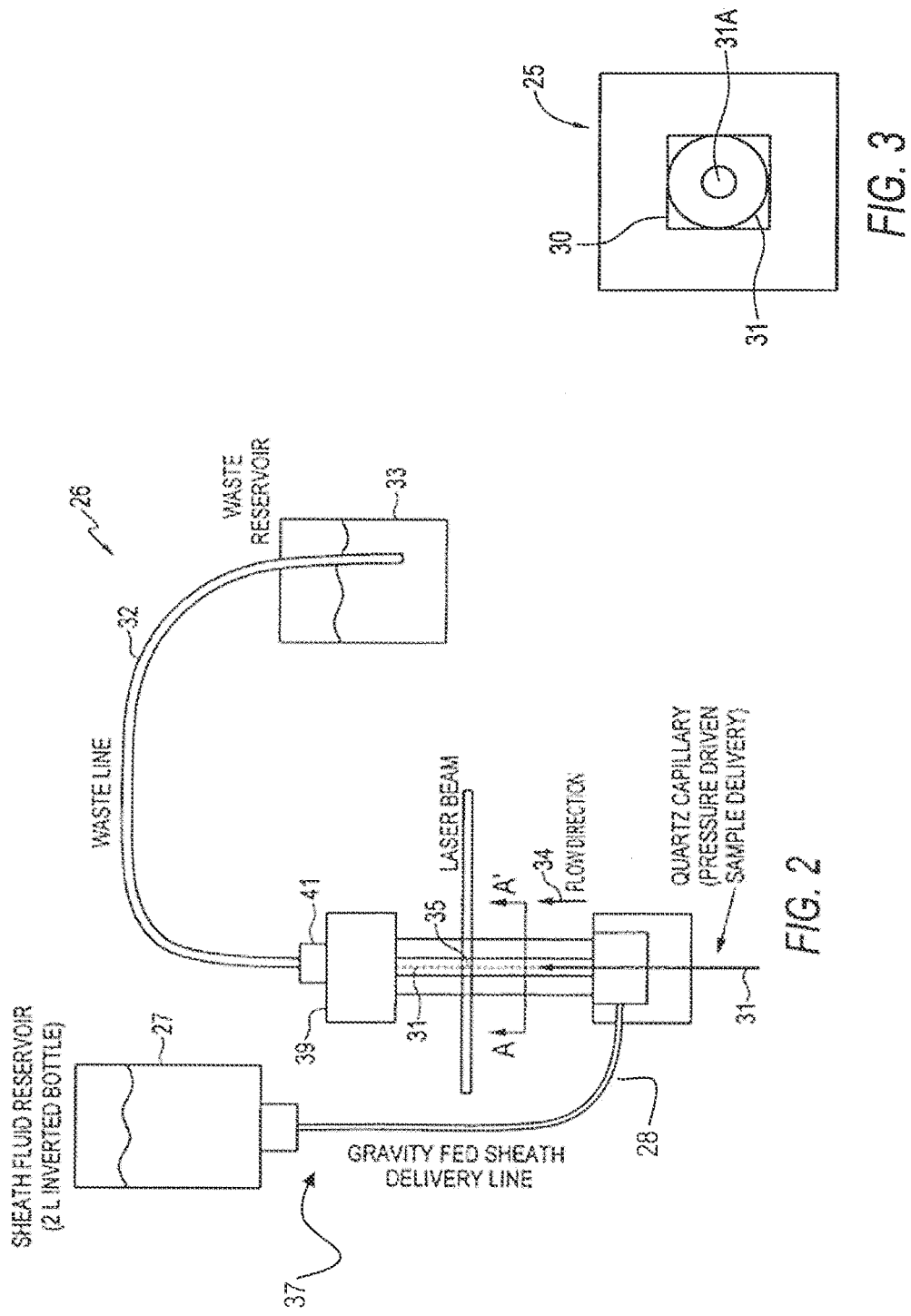

SYSTEM AND METHOD FOR MEASURING PARTICLES IN A SAMPLE STREAM OF A FLOW CYTOMETER USING A LOW POWER LASER SOURCE

CROSS-REFERENCE TO RELATED APPLICATIONS

This application is a continuation of U.S. patent application Ser. No. 11/593,312, filed on Nov. 3, 2006, the contents of which is incorporated by reference herein in its entirety.

STATEMENT OF GOVERNMENT RIGHTS

This invention was made with government support under Contract No. DE-AC52-06NA25396 awarded by the U.S. Department of Energy. The government has certain rights in the invention.

TECHNICAL FIELD

Embodiments are generally related to sensor methods and systems. Embodiments are also related to flow sensor analyzers, such as flow cytometers that move particles in a flowing fluid through a sensing region where multiple independent optical measurements are made on the particle. Embodiments are also related to portable systems for interrogating particles in sample streams of flow cytometers or the like.

BACKGROUND

Flow cytometry is a technology in which multiple physical and optical characteristics of single small or microscopic particles, such as cells or microspheres, are analyzed as they flow in a fluid stream through one or more beams of light. Flow cytometry is an integral technology in nearly every bio-medical discipline including diverse biological assays in clinical settings. Additionally, flow cytometry is an important analytical platform to perform biological point detection, bio-surveillance, and forensic analysis in support of homeland defense.

In the flow cytometer, particles are carried to the light beam intercept in a fluid stream. When particles pass through the light beam, they scatter the light and any fluorescent molecules present on or in the particle fluoresce. These resulting optical signals are directed by means of optics to appropriate detectors which generate electronic signals proportional to the optical impulses striking them. These electronic signals are processed to gather data on each particle or event and subsequently analyzed to provide information about the sample. Various particle properties, such as particle size, granularity and fluorescence intensity, can be determined by a flow cytometer recording how the particle under interrogation scatters the incident light beam and emits fluorescence.

Flow cytometers typically incorporate expensive lasers with highly stable outputs in order to obtain the high detection sensitivity and resolution necessary in many applications. Unfortunately, the size and expense of typical flow cytometers currently restricts their use to clinical and laboratory environments. Such flow cytometers cost more than 30,000 US dollars to purchase. For many potential users of flow cytometers, instrumentation size and cost are important considerations that may limit the acceptance of these systems in broader applications.

There is a continuing need to provide improved systems and methods for measuring particles in a sample stream of a flow cytometer or other flow based analyzers which can be implemented at low cost and with reduced infrastructure requirements, such as electrical power or other laboratory-based requirements. Reducing size and cost nearly always speeds acceptance and adoption of new technology.

SUMMARY

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

It is, therefore, one aspect of the present invention to provide for improved sensor methods and systems.

It is another aspect of the present invention to provide for improved methods and systems for measuring particles in a flow stream of a flow cytometer or like analyzer.

It is a further aspect of the invention to provide low cost methods and systems for measuring particles in a flow stream of a flow cytometer or other flow based analyzer.

The aforementioned aspects of the invention and other objectives and advantages can now be achieved as described herein.

According to one aspect, a system for interrogating a particle in a sample stream of a flow cytometer or the like has a laser light source for generating a low power light beam and a fluidics apparatus for transporting the particle in the sample stream at substantially low velocity resulting in extended transit times through the light beam for interrogation thereof. Also included in the system are one or more detectors for detecting optical signals resulting from the light beam impinging on the particle and signal conditioning circuitry, operably coupled to the detector(s), for conditioning output signals from the detector(s) into electronic signals for processing thereof. The signal conditioning circuitry can be a low pass filter circuitry for filtering high frequency noise from the detected optical signals.

Advantageously, the fluidics apparatus transports the particle in the sample stream at substantially low velocity through the focused laser beam resulting in extended transit times to increase sensitivity and the signal conditioning circuitry is configured to low pass filter the resulting detected optical signals, which permits high-sensitivity measurements to be made with simplified circuitry and low-cost components, such as a laser pointer and miniature detectors.

The light source can be for example a low power laser pointer module such as a diode pumped solid state (DPSS) green laser. The transit time of the particle through the light beam can be of the order of 100 microseconds or more. The low pass filter circuitry can have a maximum cut off frequency of about 10 KHz.

The detector can be for example a Photomultiplier tube (PMT), photodiode, APD or hybrid detector. The signal conditioning circuitry can comprise a pre-amplifier stage coupled to the output of a PMT detector with the low pass filter circuitry integrated in the pre-amplifier stage. The pre-amplifier can be for example a high input impedance voltage follower circuit coupled to a limited bandwidth inverting amplifier.

The fluidics apparatus can include a hydrodynamically focused flow chamber, an acoustically focused flow chamber or an unfocused flow chamber. The flow chamber can be coupled to a slow flow delivery system for transporting the particle through the light beam with the substantially low velocity resulting in extended transit times (>100 microseconds).

According to another aspect, a system for interrogating a particle in a sample stream of a flow cytometer or the like has a low powered laser pointer for generating a light beam and a fluidics apparatus for transporting the particle in the sample stream at substantially low velocity through the light beam for interrogation thereof. Also, the system includes one or more detectors for detecting optical signals resulting from the light beam impinging on the particle and signal conditioning circuitry, operably coupled to the detector(s), for conditioning output signals from the detector(s) into electronic signals for processing thereof. The signal conditioning circuitry can include low pass filter circuitry for filtering high frequency noise from the detected signals.

According to another aspect, a method for analyzing a particle in a sample stream of a flow cytometer or the like comprises generating a low power light beam; transporting the particle at substantially low velocity in the sample stream through the light beam for interrogation thereof, detecting light signals generated in response to the light beam impinging on the particle, and signal conditioning the detected light signals into electronic signals for processing thereof, the step of signal conditioning comprising filtering high frequency noise from the detected light signals.

By transporting the particle at substantially low velocity through the light beam to increase sensitivity and low passing filtering the resulting detected optical signals, high detection sensitivity and resolution can be achieved using lower power and less stable light beams than those typically used in the flow cytometers of the prior art. The system permits the use of low cost and compact lasers whilst providing the detection sensitivity and resolution demanded by many applications.

The transit time of transporting the particle through the low power light beam can be about 100 microseconds or more. The high frequency filtering has a maximum cut off frequency of about 10 KHz. The low power light beam can be generated by a laser pointer module. The low power light beam can be detected by a PMT. The step of transporting the particle can include hydro-dynamically or acoustically focusing the sample stream through a flow chamber.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

FIG. 2 illustrates the fluidic apparatus of FIG. 1 in more detail;

FIG. 3 illustrates a cross-sectional view of the flow cell taken along line A-A' of FIG. 2;

DETAILED DESCRIPTION OF ILLUSTRATIVE EMBODIMENTS

The illustrative embodiment provides an approach to interrogating microscopic particles in a sample stream of a flow cytometer, or other systems that use the flow cytometry paradigm, using a method and a system which enables a compact and inexpensive flow cytometer to be implemented, while having high detection sensitivity and resolution comparable to that of prior art flow cytometers.

Figure 1:
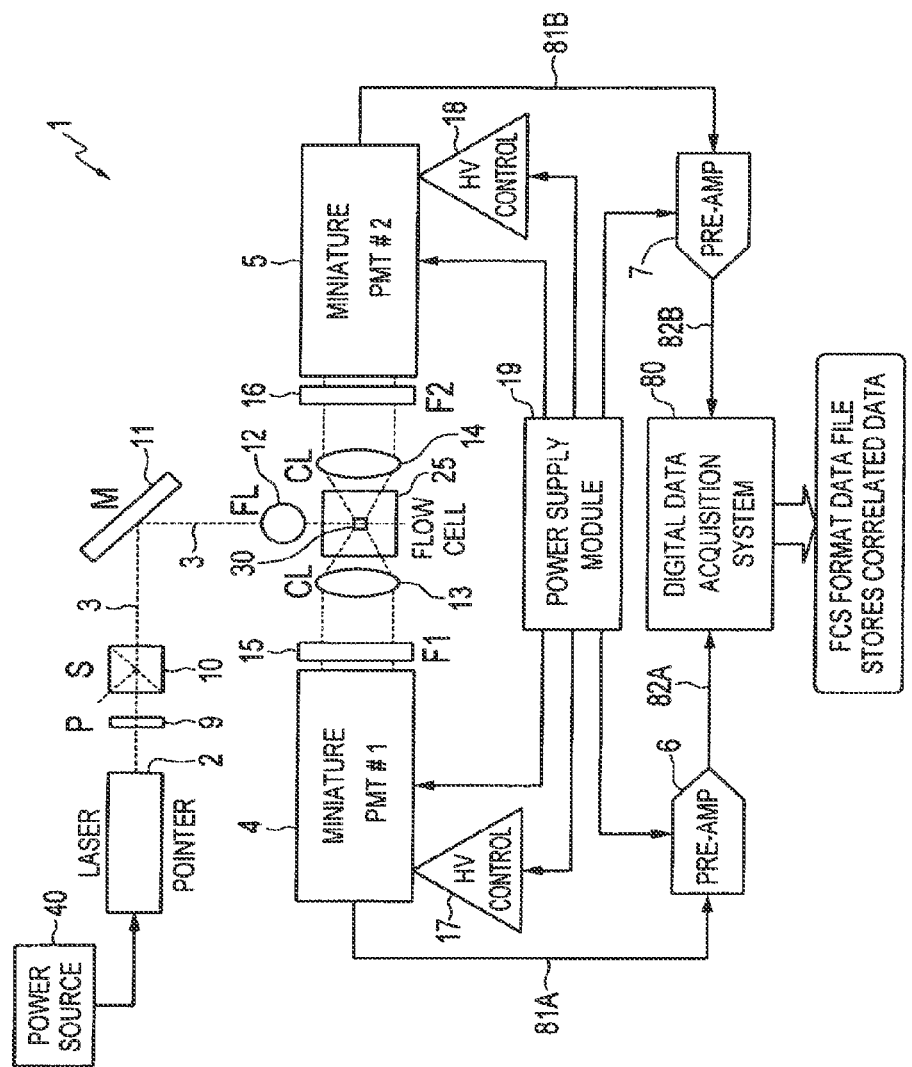
FIG. 1 illustrates a block diagram of a system for interrogating a microscopic particle in a sample stream of a flow cytometer according to a preferred embodiment.

Referring to FIGS. 1 and 2 of the accompanying drawings, which, respectively, illustrate block diagrams of the optical-electrical circuitry and fluidic circuitry of the system for measuring particles in a sample stream of a flow cytometer according to one embodiment. The system 1 has a light source 2 for generating a low powered light beam 3 and a fluidics apparatus 26, which is configured to transport particles in the sample stream 30 at a substantially low velocity through the light beam for interrogation. Detectors 4, 5 are configured to detect optical signals generated in response to the light beam 3 impinging the particles. Signal conditioning circuitry 6, 7 can be connected to each of the detectors 4, 5 to condition each detector output 81A, 81B into electronic signals 82A, 82B for processing and can be designed to generate a limited frequency response in order to filter high frequency noise from the detector output signals.

As will be explained in more detail below, configuring the system to transport particles in the sample stream at substantially low velocity through the light beam and filtering high frequency noise from the detector output using limited bandwidth signal conditioning circuitry, permits a compact and inexpensive diode pumped solid state laser to be used in a flow cytometer while maintaining high detection sensitivity and resolution using miniature detectors that require minimal support circuitry.

In the illustrative embodiment of the system of FIG. 1, the light source 2 for generating the low powered light beam is a low powered laser, typically having a 10 mW or less output. For example, the light source can be an inexpensive diode pumped solid state (DPSS) laser, such as a laser-pointer module. One example of a suitable laser pointer is an OEM version of a commercially available laser pointer (532 nm, 3.0 mW, model GMP-532-5F3-CP) from LaserMate Group, Inc. which emits a green laser beam. The laser pointer operates on 2.1-3.0 VDC and has a rated output of 3-5 mW. A power source 40, such as Tektronix power supply (model PS281), provides the DC voltage (typically 2.3 VDC @270 ma). Alternatively, a battery or very simple line-voltage operated power supply can be utilized to power the laser pointer with no observable degradation of the system performance. The laser head itself is a very compact device with reasonable manufacturer's specifications (TEM00, <1.4 mrad beam divergence, $M^2<2$, and 5% output power stability). Advantageously, the laser pointer module is inexpensive, compact and results in the entire excitation source using less than 1 W of power, which greatly increases instrument portability.

Optics 9-11 are configured to direct the laser beam 3 to the analysis region 35 of the system, that is, the point where the stream 30, which is flowing from out of the page of FIG. 1, intercepts the light beam 3. A half-wave plate 9 and polarizing beam splitter 10 positioned between the light source 2 and a mirror 11, serve to attenuate the laser beam (to the desired power level). Mirror 11 is configured to reflect the beam 3 onto a focusing lens 12, which focuses the beam to a high light flux (10 µm diameter spot) at the analytical region 35 of the system.

Detectors 4, 5, which are configured as side-scatter light (SSC) and fluorescence (FL) detectors, respectively, are aimed at the analytical region 35 of the system. Collection lenses 13, 14 are arranged on either side of the flow cell 25 to collect and concentrate light onto the detectors 4, 5 through respective filters 15 (SSC), 16 (FL).

In the illustrative embodiment of the system of FIG. 1, the detectors 4, 5 are photomultiplier tubes which detect the optical impulse generated when the particle passes through the light beam 3 and produces a current signal proportional to the intensity and duration of the impulse. The photomultiplier tubes utilized in this example are miniature Hamamatsu 5783 or 6780 Photomultiplier tubes. These multi-alkali metal-package detectors typically have a gain of about $10^6$ and radiant sensitivity of 60-80 mA/W in the 400-700 nm range, depending on the specific model used, and are operable with a high voltage of 250 to 1000V The exact voltage utilized depends on the individual PMT, the laser output power, and the intensity of the signals being measured (fluorescence or light scatter), which in turn is related to the particles being analyzed. Other low cost and compact light detectors can alternatively be employed. The detectors could be photodiodes, avalanche photodiodes or any small detector capable of detecting light emission. Utilizing low cost, compact PMTs further reduces the cost and size of the system.

Signal conditioning circuitry 6, 7 consists of pre-amplifiers connected to the anode of PMT detectors 4, 5 to provide high input impedance and limited bandwidth. The primary function of a pre-amplifier is to convert a current signal to a voltage signal for further use by data acquisition electronics. A power supply module 19 is assembled and electrically coupled to the detectors 4, 5 and signal conditioning circuitry 6, 7 to provide typically + and −5 VDC (200 ma) for the pre-amplifiers 6, 7, and +15 VDC (200 ma) to power and control the high-voltage 17, 18 for each PMT 4, 5. Further signal amplification, if needed, can be provided in a data acquisition system 80 which is coupled to the signal conditioning circuitry outputs for collection of the conditioned PMT output signals 82A, 82B.

Figure 4:
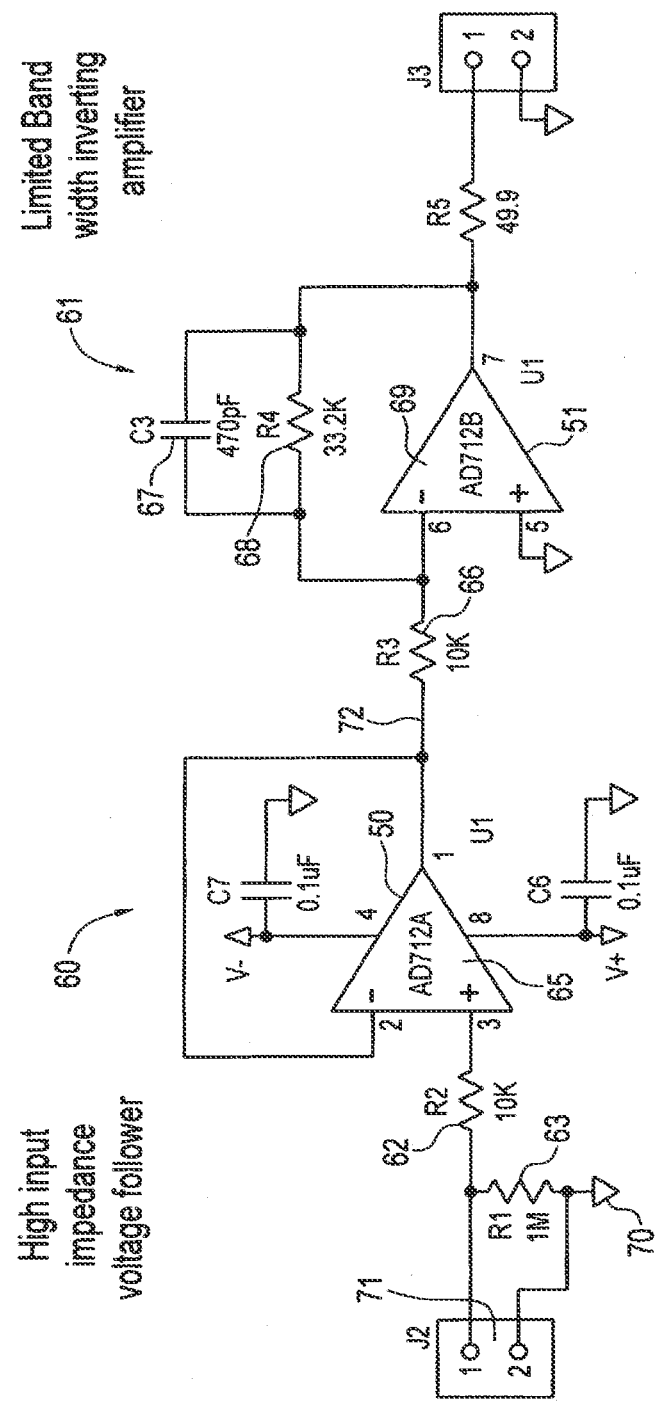
FIG. 4 illustrates a schematic circuit diagram of a high input impedance limited bandwidth pre-amplifier of the system depicted in FIG. 1.

Signal conditioning circuitry 6, 7 is designed to have limited bandwidth to filter any high-frequency noise in the PMT detector outputs. As shown in FIG. 4, which is a schematic circuit diagram of an example of the pre-amplifier circuitry, the pre-amplifier circuitry has a high input impedance voltage follower 60 coupled to a limited bandwidth inverting amplifier 61 in each of the pre-amplifiers 6, 7. The inverting amplifier 61 has an effective bandwidth of approximately 10 kHz and amplification factor of 3.3. Voltage follower 60 has a pair of resistors 62, 63 serially connected between the non-inverting input 65 of an operational amplifier 50 and ground 70 and provides high impedance to the output 71 of a respective detector 4, 5 which output is connected across resistor 63. The voltage follower output 72 is connected via input resistor 66 to the inverting input 69 of an operational amplifier 51 of the amplifier 61. A resistor 68 and capacitor 67 (RC) circuit is arranged in the feedback path of the operational amplifier between the operational amplifier output and the inverting input 69 and is selected to have an RC constant to provide a maximum cut off frequency of about 10 kHz.

Low pass filters other than the limited-bandwidth amplifier 61 can be utilized in system 1 to achieve the desired high-frequency filtering and need not necessarily be integrated in the pre-amplifier circuit. For example, the low pass filter could alternatively be implemented in signal conditioning circuitry after the pre-amplifier.

Incorporating a limited bandwidth pre-amplifier (effectively a low-pass filter) 61 in the signal conditioning circuitry is advantageous in that the high-frequency noise produced by low cost, relatively unstable light sources, such as laser pointer module, can be filtered out from the detected optical signals. By extending the transit times of the particles through the light beam to increase sensitivity and low passing filtering the resulting detected optical signals, high detection sensitivity and resolution can be achieved using lower power and less stable light beams than those typical utilized in the flow cytometers of the prior art. The system permits the use of low cost and compact lasers whilst providing the detection sensitivity and resolution demanded by many applications. Slow flow, that generates extended transit times of the particles through the focused light beam, permits high-sensitivity measurements to be made with simplified circuitry and low-cost components, such as the laser pointer and miniature detectors, to create a portable battery powered system with high performance. Both of these components have minimal power requirements which makes it possible to operate the system off of a battery or simple power supply such as a "wall wart" and 3-terminal voltage regulators with resulting performance is at least as good as the state-of-the-art systems currently available.

Figure 6:
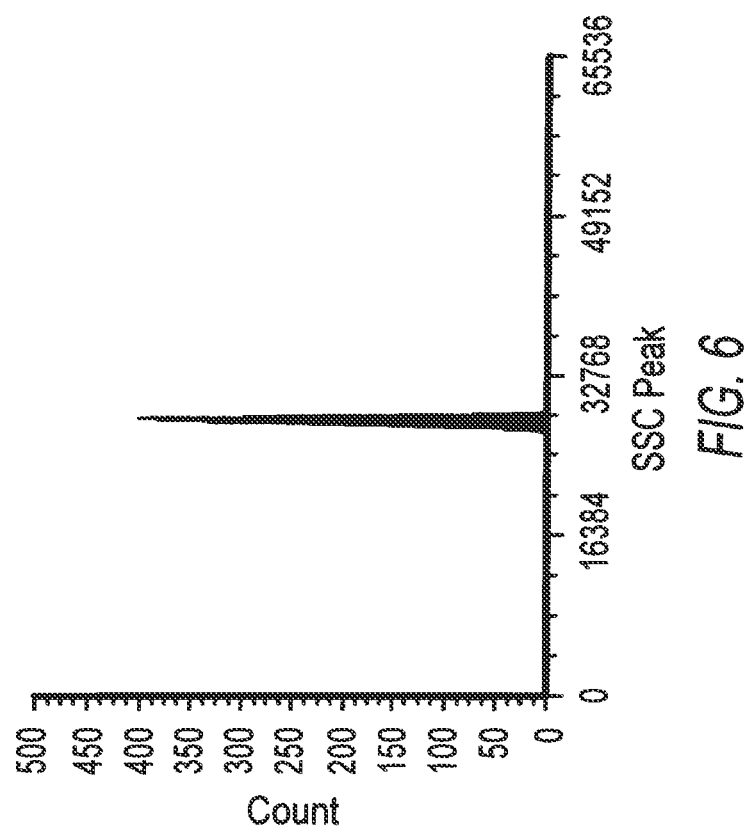
FIG. 6 illustrates a histogram of the Side Scatter (SSC) amplitude parameter on 10000 simulated events that demonstrates the stability of the laser pointer by virtue of the 1.24% coefficient of variation (CV) of the distribution.
Figure 9:
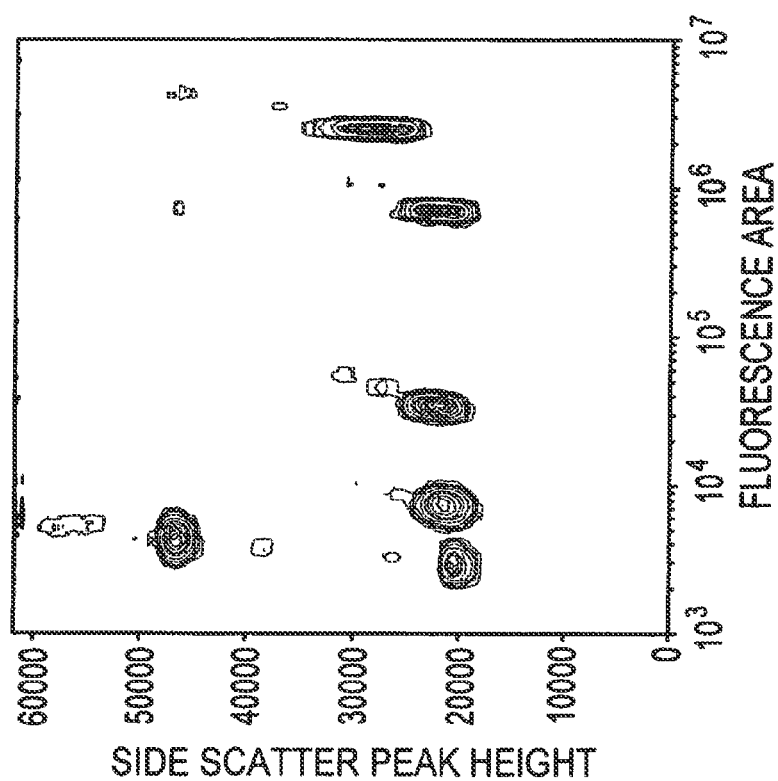
FIG. 9 illustrates high-resolution SSC performance in a contour plot of SSC peak Vs fluorescence area, obtained by analyzing a mix of 1.87 and 2.8 μm blank microspheres added to the RCP-20-5 2.1 μm diameter microsphere set using the system of FIG. 1.
Figure 10:
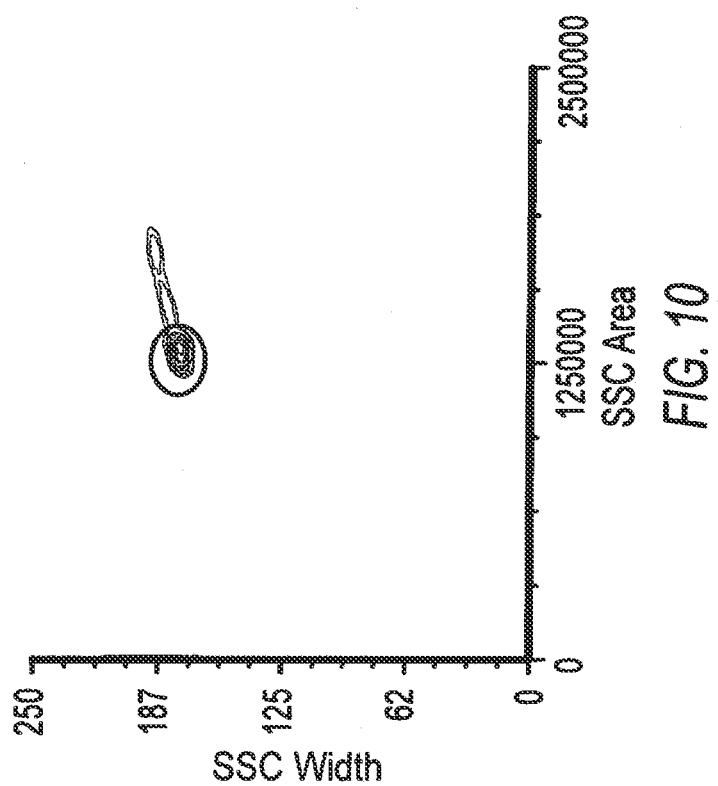
FIG. 10 displays a contour plot of SSC Peak Vs SSC Width obtained by analyzing the RCP-30-5A microsphere mixture with the system of FIG. 1, which illustrates the region of interest around the main peak used to gate the fluorescence data in FIGS. 11 and 12.

In typical flow cytometry data processing the pulse (or impulse) caused by a particle passing through the laser beam is characterized by 3 measurements: amplitude (or peak), duration, and area, and it is this correlated data collected by the data acquisition system that can be plotted as 1D histograms (as in FIG. 6). The correlated data can also be displayed in 2D as dot plots or contour plots (as in FIG. 9), or other displays depending on the software utilized. Specific regions on these plots can be sequentially separated by a series of subset extractions which are termed gates. Specific gating protocols exist for diagnostic and clinical purposes. The plots are often made on logarithmic scales.

A data acquisition system 80 is configured to collect conventional flow cytometric data files in which the event-based parameters of height, width, and area were collected from the electronic pulses derived from detectors 4, 5 and pre-amps 6, 7. Custom hardware boards are configured to convert the pre-amp output (2 V peak-to-peak) into a 14-bit digital data stream using a free running 14-bit 40 MS/sec ADC (Analog Devices—ADS5421Y). The output from each pre-amp 6, 7 is connected directly to separate ADC inputs. A field programmable gate array on the custom board captures the correlated digitized waveforms and sends them to a commercial digital signal processor board (OrSys—microline C6211CPU). The digital signal processor (Texas Instruments—TMS320C6211) extracts the pulse height, pulse area and pulse width parameters, sending the list-mode results to the host computer over FireWire (IEEE1394). The pulse parameters are recorded in FCS 3.0 data files with 24 bits for area, 16 bits for peak, 12 bits for width, and 28 bits for time (1 msec resolution). The pulse height, area and width were recorded in Flow Cytometry Standard (FCS) v.3.0 data files, which is an industry standard data file format for flow cytometry. Data acquisition techniques for flow cytometry are known in the art and will not be described in any more detail here.

Referring now in more detail to the fluidic apparatus 26 of FIG. 2, the fluidic apparatus includes a flow chamber 25, which in this particular embodiment is an optical flow cell 25, and a slow-flow sample delivery system 37 configured to pass the sample through the flow cell 25 at substantially low velocity (~5 cm/sec) such that the particles have extended transit times across the beam 3. Typically, these extended transit times are about 100 microseconds or more. Advantageously, by the fluidic apparatus extending the particles' transit times across the beam 3, the particle under interrogation has a longer residence time in the analytical region 35 thereby increasing the system detection sensitivity and resolution for a given light beam power so that relatively inexpensive miniature PMTs provide adequate performance.

The slow-flow sample delivery system 37 has gravity driven sheath flow from a sheath bottle 27, which is suspended above the flow cell 25 such that sheath fluid is fed to the flow cell via a sheath delivery line 28 connected between the lower end of the bottle and a side port of the flow cell assembly. A sample delivery tube or capillary 31 is connected to the bottom end of the flow cell 25 such that the sample to be interrogated can be delivered under pressure to the flow cell. In the center of the flow cell is a 250×250 µm square flow channel 30 and the sample delivery tube 31 occludes about 75% of the square flow channel, as best shown in FIG. 3, which illustrates a cross-sectional view of the flow cell taken along line A-A' of FIG. 2. The capillary 31 has a 40 µm inner diameter ID 31A as indicated by the white circle in FIG. 3. The capillary, with an outer diameter of 245 µm, is inserted about 5 mm into the square flow channel 30, and this occlusion results in relatively low volumetric flow rates of sheath for focusing of particles. The low sheath rate results in extended transit times through the laser beam. A waste line 32 couples the upper end of the flow channel (of the flow cell) to a waste reservoir 33 that has a fluidic head to prevent oscillation in fluid flow rates. The waste line is connected to the flow cell upper end (cuvette) 39 by a short length of soft silastic rubber tubing 41 that is gently pressed up to the top of the cuvette and held in place by a metal arm. By adjusting the relative heights of the sheath supply bottle 27 and the waste reservoir 33, the transit time of single particles across the laser beam 3 can be varied from about 100 microseconds to milliseconds. The direction of flow in the flow cell is from bottom to top to help clear bubbles, as show in FIG. 2, and flowing out of the page in FIG. 1. The sample is introduced through the sample tube 31 and into flow cell 25 for focusing via the sheath stream. The sample is pushed in via pressure, while the sheath is gravity fed in the corners of the flow channel around the capillary. The sheath bottle can be raised above the flow cell (for gravity delivery) and pressurized to set the transit time.

In the illustrative embodiment of the system of FIG. 1, the flow cell 25 is a hydrodynamically focused flow cell. However, any particle focusing technique (e.g. acoustic, dielectrophoretic, etc. . . . ) that results in extended transit times (100 microseconds to milliseconds) can be employed. Furthermore, any flow chamber suitable for passing the sample stream through the light beam could be employed. All that is required is that the particle passes (centered in the flow channel) through the light beam 3 with sufficiently slow velocity so that the low powered light beam striking the particle results in optical signals which are detectable with sufficiently high sensitivity to enable the use of low powered laser beams.

A method 100 for interrogating a particle in a sample stream of a flow cytometer according to one embodiment will now be described with reference to FIG. 5 which is a flow diagram outlining the steps of the method 100. The method 100 can, for example, be implemented in the system of FIG. 1. As a general overview, initially a light beam is generated as indicated in step 101 of FIG. 5. In the system of FIG. 1, the light beam 3 is a low power light beam generated from a laser power module. The particle is transported in a sample stream through the generated light beam at substantially low velocity (step 102). For example, this step can be implemented in the system of FIG. 1 by hydro-dynamically or acoustically focusing the sample stream through the flow cell 25 and delivering the sample using the slow flow delivery system 37 to transport the particle through the laser beam 3 with a velocity which is sufficiently low to extend the transit time of particle through the light beam to about 100 microseconds or more.

Figure 5:
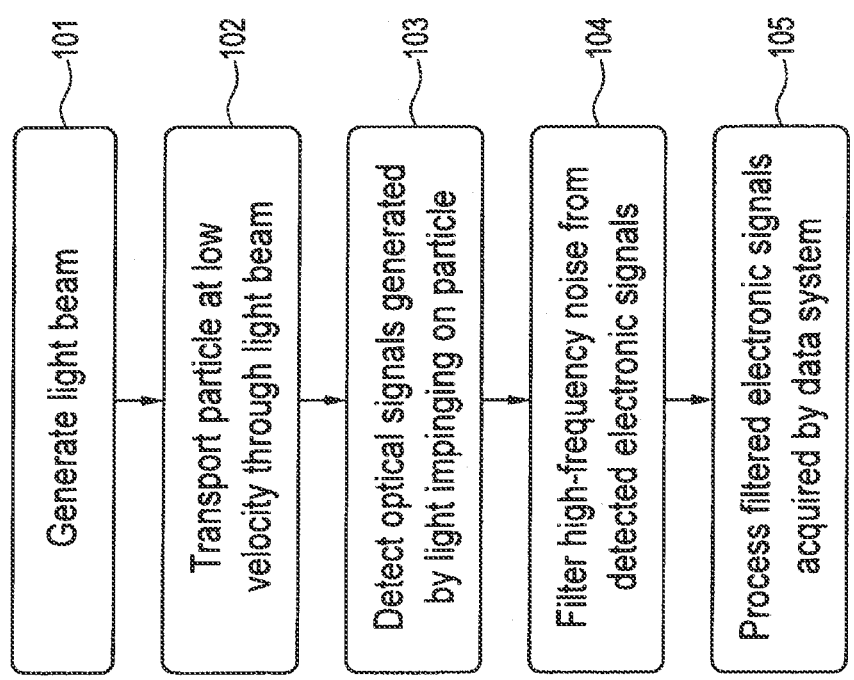
FIG. 5 illustrates a flow diagram outlining a method for interrogating a particle in a sample stream of a flow cytometer according to a preferred embodiment.

Thereafter, optical signals, generated in response to the light beam impinging on the particle, are detected (step 103 of FIG. 5). This latter step can be performed by the PMT detectors 4, 5 of the system of FIG. 1. High frequency noise is then filtered from the detected light signals (step 104) for processing (step 105). In the system of FIG. 1, step 104 is implemented by means of the limited bandwidth inverting amplifier 61 of the signal conditioning pre-amp and step 105 is performed by the data acquisition system of the system of FIG. 1.

EXPERIMENTAL EXAMPLES AND RESULTS

Specific results that have been obtained using the system and method of interrogating a particle in a sample stream of a flow cytometer according to the illustrative embodiments will now be described in which the interrogated samples were fluorescent calibration microsphere sets. The microsphere samples were concentrated 5-10× via centrifugation prior to use to compensate for the volumetric flow rate in this example (~0.3-0.6 µl/minute) due to the narrow bore (40 µm ID) quartz capillary tubing utilized to deliver the sample to the flow cell. All microsphere samples were purchased from Spherotech Inc. (Libertyville, Ill.), and included: Rainbow Calibration Particles RCP-30-5A (8 peaks), RCP-20-5 (4 peaks), CP-15-10 (blank 1.87 µm dia.), and CP-25-10 (blank 2.8 µm dia.). The specific type used is given in the text for each example.

In these examples, the laser 2 was the aforementioned green laser pointer module (532 nm, 3.0 mW, model GMP-532-5F3-CP) from LaserMate Group. The miniature Hamamatsu PMTs described above were employed as detectors 4, 5, which were mounted in optical tubes that held bandpass filters 14, 15 and the light collection lenses 12, 13 in a light-tight assembly surrounding the flow cell 25. The high NA aspheric lenses 12, 13 collected light from the flow cell, which was passed through band pass filters to the detectors 4, 5. A 515-545 nm band pass filter was used in the side-scatter (SSC) light channel while a 565-605 nm band pass filter was used in the fluorescence channel.

In these examples, high purity water served as the sheath fluid which was gravity fed from a 2-L sheath bottle 27 suspended about 20 cm above the flow cell 25, which was a 2 cm long fused-silica cuvette 2.5×2.5 mm cross-section with a 250×250 μm flow channel. Polyethylene tubing (0.75 mm ID, about 1.5-m long) was utilized as the waste line 32. A 3-m long continuous column of water, from the sheath bottle 27 to the waste reservoir 33, stabilized the slow flow through the gravity-driven system. Sample solutions were driven from a 0.5-ml Eppendorf tube by nitrogen gas pressure through the sample delivery tube 31 which was a Polymicro Technologies (Phoenix, Ariz.;) fused silica capillary tube (40 μm ID, 245 μm outer diameter (OD), ~30-cm long) inserted 4-5 mm into the 250 μm square channel of the flow cell. Sheath fluid flowed around the capillary, in the corners of the channel, vertically (from bottom to top in FIG. 2; out of the page, in FIG. 1), which facilitated dislodging bubbles from the flow cell. The inserted tip of the capillary, ground to a 14° taper by New Objective, Inc. (Cambridge, Mass.), is positioned 300 μm below the interrogation region 35. The small-bore capillary served two purposes. First, it predisposed the fluidic system to slow-flow because it occluded about 75% of the flow channel. Second, its flow resistance permitted control of the sample delivery rate with a sensitive electronic pressure regulator (MiniPR-NC-1500-5-NR; Redwood Microsystems, Menlo Park, Calif.). The elevated sheath bottle 27 was pressurized to provide ~2 psig in order to reach a transit time of about 250 microseconds.

The combination of scattered and fluorescent light was collected by the collection lenses 12, 13, filtered by filters 14, 15 and picked up by the detectors 4 (SSC) 5 (Fluorescence), and fluctuations in brightness at each detector were converted to electrical signals which were conditioned by the signal conditioning circuitry, analogue to digital converted and then processed into data. FCS files were analyzed using FCS Express from DeNovo Software.

Figure 7:
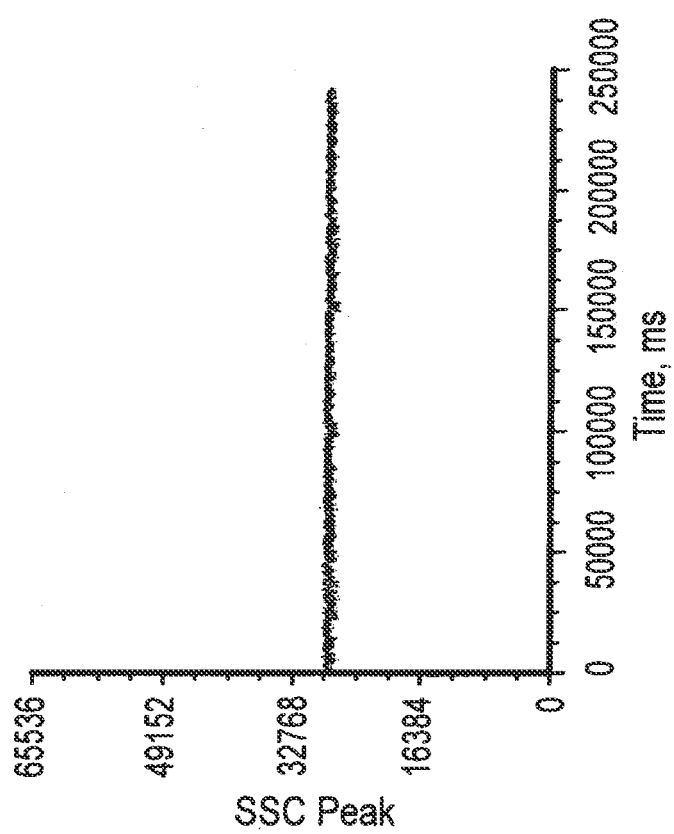
FIG. 7 demonstrates the stability of the laser pointer by displaying SSC peak (amplitude) versus time during the entire 4 minutes required to collect 10000 simulated events.

Laser stability was first measured by slightly misaligning the flow cell so that some of the laser light was refracted into the SSC detector pathway (without any particles in the flow channel). The data acquisition system 80 was electronically triggered to collect 10000 simulated events, recording the pulse height, width and area measurements from the SSC channel. These results, depicted in FIG. 6, indicate that the laser output was stable during the data collection interval and the precision of the measurements is indicated by the coefficient of variation (CV) of the histogram peak, which was 1.24% for both SSC Peak and SSC Area. The laser stability over time is clearly shown by the stability of the scattered light over 4 minutes of collection (FIG. 7).

Figure 8:
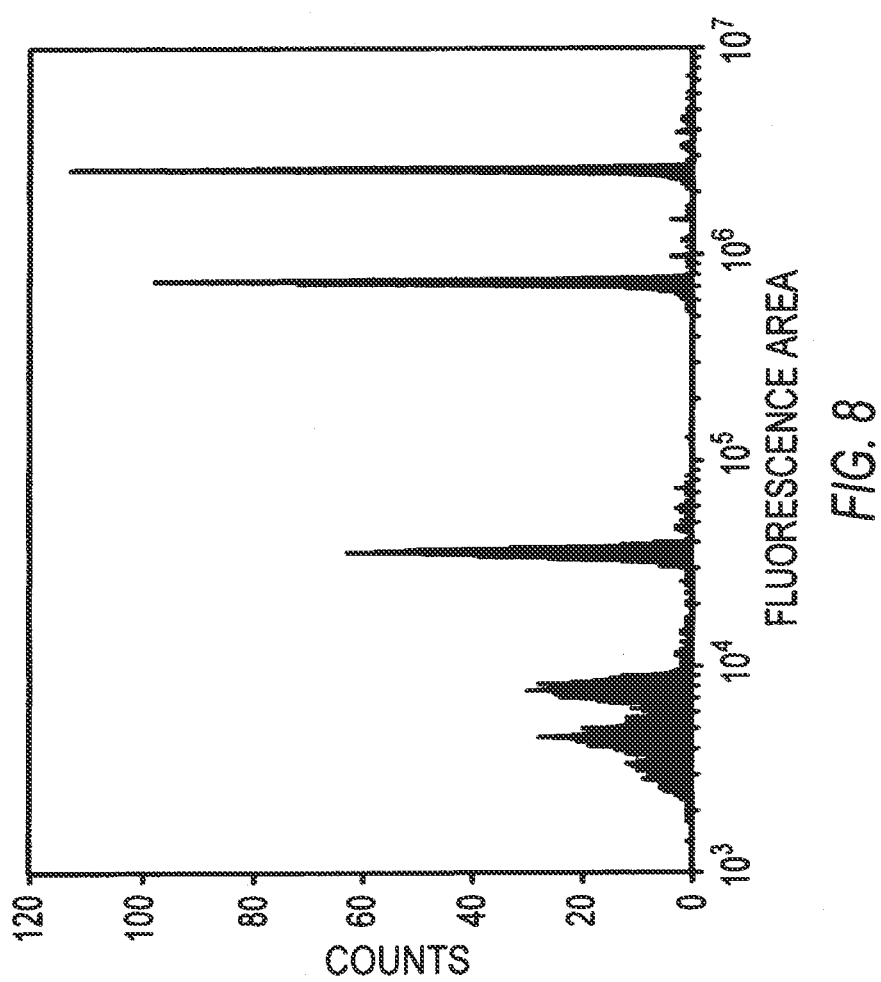
FIG. 8 illustrates high-resolution and high-sensitivity performance on 6 populations of microspheres in the fluorescence area histogram, obtained by analyzing a mix of 1.87 and 2.8 μm blank (i.e. non-fluorescent) microspheres added to the RCP-20-5 2.1 μm diameter microsphere set using the system of FIG. 1.

The pulse data for a series of microspheres were collected using the data acquisition system 80. FIG. 8 demonstrates excellent resolution and sensitivity obtained from analyzing a mixture of the 4 population set of RCP-20-5 microspheres with non-fluorescent 1.9 μm (CP-15-10) and 2.8 μm (CP-25-10) polystyrene microspheres added. The three dimmest microspheres that are not well resolved in the Fluorescence Area histogram (below $10^4$) of FIG. 8, are completely resolved in the contour plot of FIG. 9, a 2D display of SSC versus Fluorescence Area.

Figure 11:
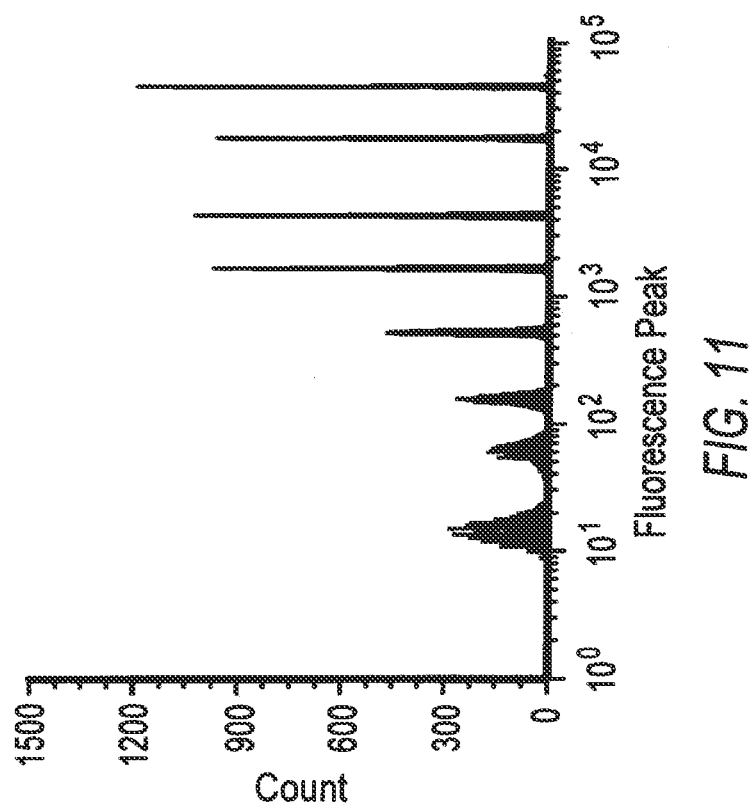
FIG. 11 illustrates excellent resolution of all 8 microsphere populations (in the 16-bit fluorescence peak data) obtained by analyzing the RCP-30-5A microspheres sample using the system of FIG. 1.
Figure 12:
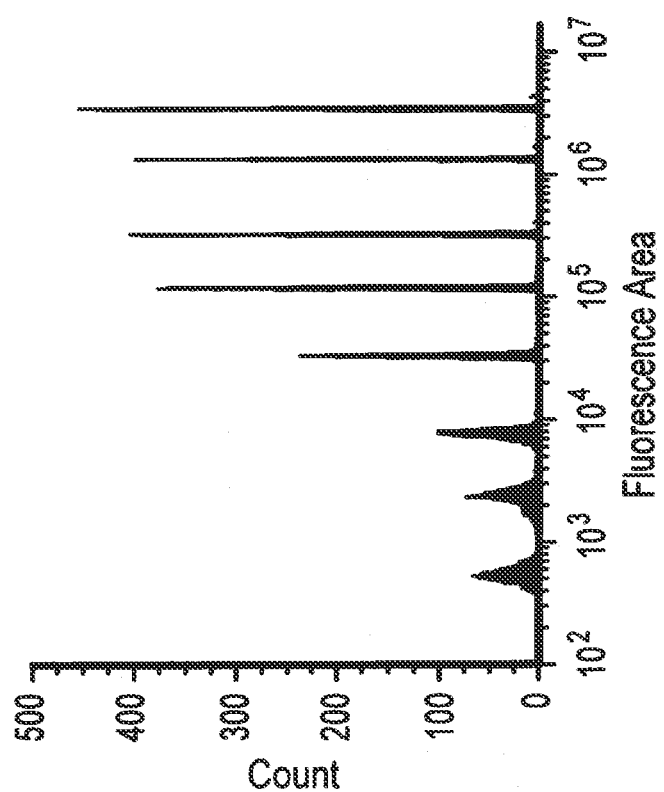
FIG. 12 illustrates excellent resolution of all 8 microsphere populations (in the 32-bit area data) obtained by analyzing the RCP-30-5A microspheres sample using the system of FIG. 1.
Figure 13:
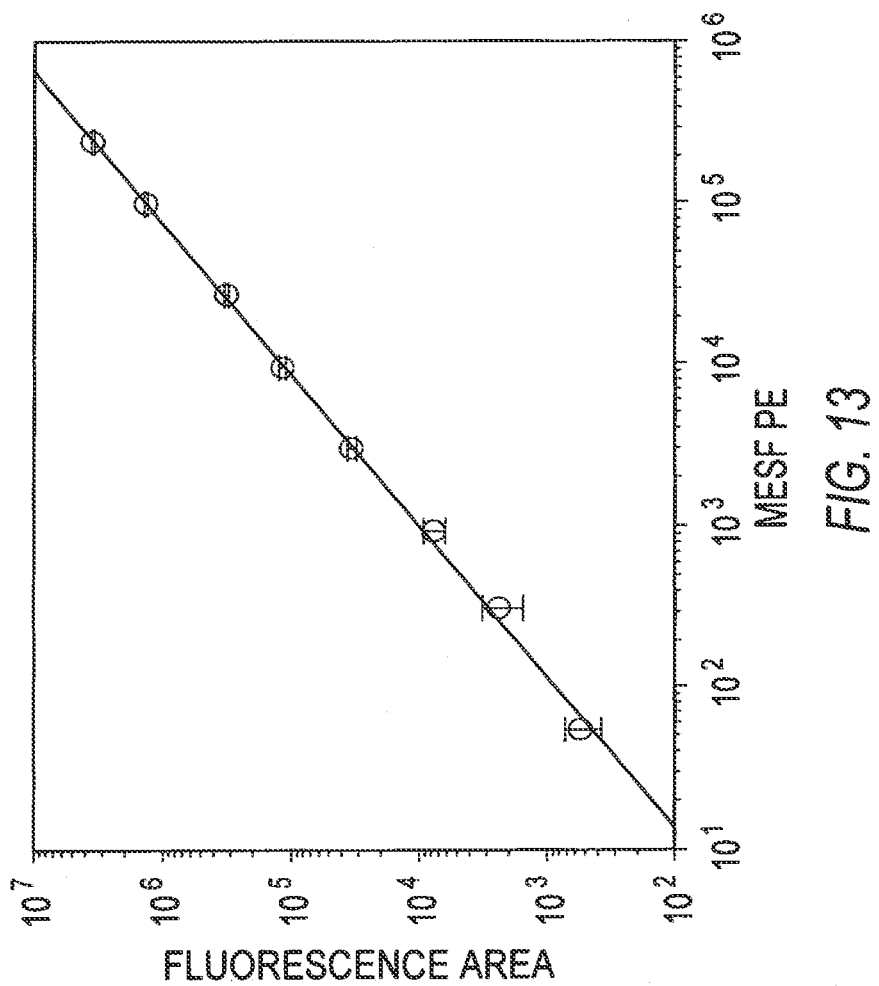
FIG. 13 demonstrates the linearity of the system in a graph of fluorescence area Vs the calibrated intensity of the RCP-30-5A microspheres (in units of Mean Equivalent Soluble Fluorophore for phycoerythrin MESF-PE) obtained by measuring the RCP-30-5A microspheres using the system of FIG. 1.

The data depicted in FIGS. 10-13 resulted from analyzing the RCP-30-5A microsphere mix with the system depicted in FIG. 1. SSC width versus SSC area are displayed in a contour plot to indicate the gating region used to identify the individual microspheres (see FIG. 10), which are then presented in 1D histograms in FIGS. 11 and 12. FIG. 11 shows baseline resolution of all 8 microsphere populations using the amplitude parameter. FIG. 12 displays exemplary data on the area parameter with all 8 populations baseline resolved over a span of 5 orders of magnitude. As shown in FIG. 13, plotting the means of the fluorescence area peaks (the means for the 8 populations) against the estimated mean equivalent soluble fluorophore (MESF) values measured in units Phycoerythrin (MESF-PE) molecules, provided by the manufacturer, demonstrates the excellent linearity and sensitivity of the system. Extrapolating from this linear fit of fluorescence vs. MESF PE suggests that the system can detect as few as 50 fluorophores of PE per particle.

The components of the system in this example (laser pointer, PMTs and aspheric lenses for focusing and collection optics) cost approximately $1000. Using 1 mW of laser power through the system to analyze RCP-30-5A microspheres resulted in baseline resolution of all 8 peaks and demonstrated detection of ~50 fluorophores per particle. With the exception of particle analysis rate and number of parameters, this experimental example of the system has demonstrated comparable performance to that of flow cytometers that use expensive lasers and detectors that cost >$10,000 using components that cost less than $1000.

The aforementioned experimentation and results are for illustration purposes only and are not intended in any way to limit embodiments of the system or method to such an example. The system and method of the illustrative embodiments could be implemented in a range of different applications, such as biomedical diagnostics, homeland defense and point of care devices, to measure other particles and particle parameters. Examples of such particles and measuring parameters are volume and morphological complexity of cells cell pigments, DNA (cell cycle analysis, cell kinetics, proliferation etc.), RNA, chromosome analysis and sorting (library construction, chromosome paint), proteins, cell surface antigens (CD markers), intracellular antigens (various cytokines, secondary mediators etc.), nuclear antigens, enzymatic activity, pH, intracellular ionized calcium, magnesium, membrane potential, membrane fluidity, apoptosis (quantification, measurement of DNA degradation, mitochondrial membrane potential, permeability changes), cell viability, monitoring electropermeabilization of cells, oxidative burst, characterizing multi-drug resistance (MDR) in cancer cells, glutathione, various combinations (DNA/surface antigens etc.). Other examples of such particles and measuring parameters are pollen, spores, paint pigment particles, plankton, and other small or microscopic organisms.

The embodiments and examples set forth herein are presented to best explain the present invention and its practical application and to thereby enable those skilled in the art to make and utilize the invention. Those skilled in the art, however, will recognize that the foregoing description and examples have been presented for the purpose of illustration and example only.

Other variations and modifications of the present invention will be apparent to those of skill in the art, and it is the intent of the appended claims that such variations and modifications be covered. For example, in the illustrative embodiment of the system 1 depicted in FIG. 1, a single laser is employed to provide a light beam 3 and a pair of detectors 4, 5 are arranged to detect side scatter and fluorescence. However, the system can have a single detector or more than two detectors and/or more than one laser as required. Furthermore, whilst the system of the illustrative embodiment is arranged to measure a plurality of particles passing through the light beam in succession, as is known in flow cytometer technology, the system could alternatively be configured to simply measure a single particle. Those skilled in the art would also understand that the system and method for analyzing a particle in a sample stream can be implemented in flow based analyzers other than flow cytometers.

The description as set forth is not intended to be exhaustive or to limit the scope of the invention. Many modifications and variations are possible in light of the above teaching without departing from the scope of the following claims. It is contemplated that the use of the present invention can involve components having different characteristics. It is intended that the scope of the present invention be defined by the claims appended hereto, giving full cognizance to equivalents in all respects.

What is claimed:

1. A particle interrogation system comprising:
   a flow chamber;
   a fluid container in connection with the flow chamber, the fluid container configured to deliver a gravity fed fluid to the flow chamber;
   a laser source configured to impinge a laser beam on one or more particles flowing in the flow chamber, wherein the laser source has a power of less than 10 mW;
   a particle delivery conduit operably coupled to the flow chamber and configured to deliver a sample fluid containing one or more particles into the flow chamber;
   at least one detector configured to receive one or more optical signals resulting from fluorescence or light scattered from the one or more particles; and
   signal conditioning circuitry, operably coupled to the at least one detector,
   wherein the flow chamber is rectangular and wherein the particle delivery system comprises a cylinder, a length of the cylinder being inserted into the flow chamber.

2. The system of claim 1, wherein the laser source comprises a non-stabilized compact laser.

3. The system of claim 1, wherein the fluid container is connected to the flow chamber via a gravity fed sheath delivery line.

4. The system of claim 1, wherein the signal conditioning circuitry comprises low filter circuitry with a maximum cut off frequency of about 10 kHz.

5. The system of claim 4, wherein the signal conditioning circuitry comprises a pre-amplifier stage coupled to the output of the detector, and wherein the low pass filter circuitry is integrated in the pre-amplifier stage.

6. The system of claim 1, wherein the flow chamber is one or more of a hydrodynamically focused flow chamber, an acoustically focused flow chamber or an unfocused flow chamber.

7. A method for interrogating one or more particles in a flow chamber, the method comprising:
   receiving from a fluid container a gravity based flow of a sheath fluid;
   flowing the sheath fluid in a flow chamber;
   delivering a sample fluid including one or more particles in the flow chamber;
   flowing, at a velocity, the one or more particles through a laser beam impinging on the one or more particles flowing in the flow chamber, the laser beam having a power of less than 10 mW;
   detecting scattered light or fluorescence resulting from the laser beam impinging on the one or more particles; and
   signal conditioning the scattered light or fluorescence into electronic signals for processing thereof,
   wherein the flow chamber is rectangular and wherein the particles are delivered to the flow chamber by a cylindrical capillary, a length of the cylindrical capillary being inserted into the flow chamber.

8. The method of claim of claim 7, wherein signal conditioning comprises filtering high frequency noise from the detected scattered light or fluorescence.

9. The method of claim 7, wherein the gravity based flow of fluid is received via a gravity fed sheath delivery line.

10. The method of claim 9, wherein a rate of flow of the sheath fluid is determined by adjusting a relative height between the fluid container and a waste reservoir.

11. The method of claim 7, wherein the scattered light or fluorescence is detected by at least one of a PMT photodiode, an avalanche photodiode (APD) or a hybrid detector.

12. The method of claim 7, wherein the laser beam is generated by a non-stabilized compact laser.

13. The method of claim 7, further comprising hydrodynamically or acoustically focusing the sample fluid flowing in the flow chamber.

14. The method of claim 7, further comprising adjusting the velocity of the one or more particles based on the power output of the laser source.

15. A particle interrogation apparatus comprising:
   a flow chamber;
   a sheath fluid container attached to the flow chamber via a gravity fed sheath delivery line, the sheath fluid container configured to deliver a gravity based flow of a fluid to the flow chamber;
   a particle delivery conduit configured to deliver a sample fluid including one or more particles into the flow chamber;
   a laser source configured to impinge a laser beam on the one or more particles in the flow stream, the laser source having a power output of less than 10 mW; and
   at least one detector configured to receive optical signals resulting from the laser source impinging on the one or more particles
   wherein the flow chamber is rectangular and wherein the particle delivery system comprises a cylinder, a length of the cylinder being inserted into the flow chamber.

* * * * *